(12) United States Patent
Takada et al.

(10) Patent No.: US 12,013,389 B2
(45) Date of Patent: Jun. 18, 2024

(54) METHOD OF EVALUATING PATHOLOGICAL CONDITIONS OF HEART FAILURE

(71) Applicant: NATIONAL UNIVERSITY CORPORATION HOKKAIDO UNIVERSITY, Hokkaido (JP)

(72) Inventors: Shingo Takada, Sapporoshi (JP); Satoshi Maekawa, Sapporoshi (JP); Takashi Yokota, Sapporoshi (JP); Ryosuke Shirakawa, Sapporoshi (JP); Hisataka Sabe, Sapporoshi (JP)

(73) Assignee: NATIONAL UNIVERSITY CORPORATION HOKKAIDO UNIVERSITY, Hokkaido (JP)

( * ) Notice: Subject to any disclaimer, the term of this patent is extended or adjusted under 35 U.S.C. 154(b) by 125 days.

(21) Appl. No.: 17/276,782

(22) PCT Filed: Jun. 28, 2019

(86) PCT No.: PCT/JP2019/025885
§ 371 (c)(1),
(2) Date: Mar. 16, 2021

(87) PCT Pub. No.: WO2020/059242
PCT Pub. Date: Mar. 26, 2020

(65) Prior Publication Data
US 2021/0349079 A1    Nov. 11, 2021

Related U.S. Application Data

(60) Provisional application No. 62/733,662, filed on Sep. 20, 2018.

(51) Int. Cl.
*G01N 33/50*   (2006.01)
*A61K 31/197*  (2006.01)
*A61K 31/7076* (2006.01)

(52) U.S. Cl.
CPC ....... *G01N 33/5091* (2013.01); *A61K 31/197* (2013.01); *A61K 31/7076* (2013.01)

(58) Field of Classification Search
None
See application file for complete search history.

(56) References Cited

FOREIGN PATENT DOCUMENTS

JP    2007008845 A   1/2007

OTHER PUBLICATIONS

Kolwicz Jr, Stephen C., Sophia Airhart, and Rong Tian. "Ketones step to the plate: a game changer for metabolic remodeling in heart failure?." Circulation 133.8 (2016): 689-691.*
Bedi Jr, Kenneth C., et al. "Evidence for intramyocardial disruption of lipid metabolism and increased myocardial ketone utilization in advanced human heart failure." Circulation 133.8 (2016): 706-716.*
Inoue, Keiji, et al. "Oral 5-aminolevulinic acid mediated photodynamic diagnosis using fluorescence cystoscopy for non-muscle-invasive bladder cancer: a randomized, double-blind, multicentre phase II/III study." Photodiagnosis and photodynamic therapy 12.2 (2015): 193-200.*
Sommera, Sebastian-Patrick, et al. "Glycine preconditioning to ameliorate pulmonary ischaemia reperfusion injury in rats." (2012).*
Bai et al., "Succinylation as a novel mode of energy metabolism regulation during atrial fibrillation," Sep. 2018. Medical Hypotheses, v. 121: 54-55.
European Office Action dated May 4, 2022 in European Application No. 19863496.6, 11 pages.
Nagao et al., "Beta-Hydroxybutyrate elevation as a compensatory response against oxidative stress in cardiomyocytes," May 2016. Biochemical and Biophysical Research Communications. 475(4): 322-328.
Zhang et al., "Accumulation of Succinate in Cardiac Ischemia Primarily Occurs via Canonical Krebs Cycle Activity," May 2018. Cell Reports, 23(9): 2617-2628.
Kenneth C. Bedi Jr et al., Evidence for Intramyocardial Disruption of Lipid Metabolism and Increased Myocardial Ketone Utilization in Advanced Human Heart Failure, Circulation, 2016, vol. 133, pp. 706 to 716, 11 pages.
English translation of International Search Report dated Sep. 24, 2019, from corresponding PCT Application No. PCT/JP2019/025885, 8 pages.
Satoshi Maekawa, Studies on determination of regulatory factor of mitochondrial function and the development of new therapy based on the mitochondrial function in heart failure, Hokkaido University Dissertations, 2019, 3 pages.
European Office Action dated May 24, 2023 in European Application No. 23159752.7, a corresponding foreign appplication of U.S. Appl. No. 17/276,782, 10 pages.
Coluccia et al., "Chronic Heart Failure is Characterized by Altered Mitochondrial Function and Structure in Circulating Leucocytes," Oncotarget, Oct. 2018, 9(80):35028-35040.
Database EMBASE Accession No. EMB-627104107—Shirakawa et al., "Excessive Mitochondrial Reactive Oxygen Species Emission from Circulating Blood Cells is Associated with Systemic Oxidative Stress, Severity of Heart Failure, and Exercise Intolerance," XP093047339, Nov. 2018, 2 pages.

(Continued)

*Primary Examiner* — Patrick T Lewis
(74) *Attorney, Agent, or Firm* — Lee & Hayes, P.C.

(57) ABSTRACT

The present invention provides a method of evaluating pathological conditions of heart failure based on a new mechanism of action of heart failure, a method of evaluating a candidate compound for a heart failure treatment drug using the mechanism of action, and a pharmaceutical composition for treating or preventing heart failure using the mechanism of action. That is, the present invention provides a method of evaluating pathological conditions of heart failure including measuring an amount of succinyl-CoA in cardiomyocytes collected from a test animal, a respiratory capacity of mitochondrial complex II in peripheral blood mononuclear cells collected from the test animal or an amount of reactive oxygen species released from peripheral blood mononuclear cells collected from the test animal; and evaluating the onset of heart failure of the test animal or the severity of heart failure based on the obtained measurement values.

8 Claims, 17 Drawing Sheets

(56) References Cited

OTHER PUBLICATIONS

European Office Action and Search Report in European Application No. 19863496.6, a corresponding foreign appplication of U.S. Appl. No. 17/276,782, dated May 24, 2023, 10 pages.
Shirakawa et al. "Excessive Mitochondrial Reactive Oxygen Species Emission from Circulating Blood Cells is Associated with Severity of Heart Failure and Exercise Intolerance", European Heart Journal, Aug. 2018, 3143, 39:643-644.

* cited by examiner

[ * p<0.05 vs. Control ]

* $p<0.05$

METHOD OF EVALUATING PATHOLOGICAL CONDITIONS OF HEART FAILURE

This application is a US national phase of PCT/JP2019/025885, filed Jun. 28, 2019, which claims priority to U.S. Provisional Application No. 62/733,662, filed Sep. 20, 2018, the content of which are incorporated herein by reference.

TECHNICAL FIELD

The present invention relates to a method of evaluating pathological conditions of heart failure, a method of evaluating a candidate compound for a heart failure treatment drug, and a pharmaceutical composition used for treating or preventing heart failure.

BACKGROUND ART

Mitochondria play an essential role in production of energy, and ATP is produced by oxidative phosphorylation. Mitochondrial oxidative phosphorylation is performed by complexes I, II, III, and IV which constitute an electron transport chain and complex V which is an ATP synthase. Among the complexes used for mitochondrial oxidative phosphorylation, the complexes I, III, and IV constitute supercomplexes (SCs) which are assembled complexes. Complex II is a protein also called succinate dehydrogenase (SDH) and is composed of four subunits (SDHA, SDHB, SDHC, and SDHD). Complex II is a protein having unique characteristics that it is a protein involved in both the TCA cycle and the electron transport chain, and among proteins constituting the electron transport chain, it is the only protein having no function as a proton pump, and it does not include a protein encoded in mitochondrial genomes.

Myocardial infarction results in development of heart failure, which is a main cause of death in patients after myocardial infarction. Mitochondrial dysfunction, that is, change in the left ventricular shape and reduced ATP production based on remodeling, contributes to development of cardiac dysfunction in heart failure after myocardial infarction. It has been reported that the amount of heme and ketone bodies synthesized increases in heart failure because oxygen and ATP are required in the non-infarct segment of the left ventricle (refer to Non Patent Literature 1). An important enzyme required for this synthesis is succinyl-CoA. Succinyl-CoA has an important role for providing succinic acid to mitochondrial complex II in the TCA cycle. Although it has been reported that the amount of succinyl-CoA is reduced in heart failure (refer to Non Patent Literature 1), the roles of succinyl-CoA and mitochondrial complex II in heart failure are still unclear.

CITATION LIST

Non Patent Literature

[Non Patent Literature 1]
  Bedi et al., Circulation, 2016, vol. 133, pp. 706-716.

SUMMARY OF INVENTION

Technical Problem

An object of the present invention is to provide a method of evaluating pathological conditions of heart failure based on a new mechanism of action of heart failure, a method of evaluating a candidate compound for a heart failure treatment drug using the mechanism of action, and a pharmaceutical composition for treating or preventing heart failure using the mechanism of action.

Solution to Problem

The inventors found that, in heart failure model mice after myocardial infarction, myocardial mitochondrial function decreased in a function-dependent manner with respect to mitochondrial complex II, this decrease involved a reduced amount of succinyl-CoA, and when succinyl-CoA was administered to isolated mitochondria of heart failure model mice, mitochondrial functions improved, and thus completed the present invention. In addition, the inventors found that, in chronic heart failure, a respiratory capacity (oxidative phosphorylation) of mitochondrial complex II of peripheral blood mononuclear cells (PBMC) is lower and the amount of reactive oxygen species (ROS) released from PBMC is larger in a severely-ill patient group than a mildly-ill patient group, and it is possible to evaluate the severity of heart failure using these as indicators, and thus completed the present invention.

Specifically, the present invention is as follows.

[1] A method of evaluating pathological conditions of heart failure, including: measuring an amount of succinyl-CoA in cardiomyocytes collected from a test animal, and a respiratory capacity of mitochondrial complex II in peripheral blood mononuclear cells collected from the test animal or an amount of reactive oxygen species released from peripheral blood mononuclear cells collected from the test animal; and evaluating the onset of heart failure of the test animal or the severity of heart failure based on the obtained measurement values.

[2] The method of evaluating pathological conditions of heart failure according to [1], wherein, when it is unknown whether the test animal has heart failure and the amount of succinyl-CoA in cardiomyocytes collected from the test animal is measured, and the obtained measurement value is less than a predetermined reference value, it is evaluated that the test animal has a high likelihood of the onset of heart failure.

[3] The method of evaluating pathological conditions of heart failure according to [1], wherein, when the test animal is confirmed to have heart failure and the respiratory capacity of mitochondrial complex II in peripheral blood mononuclear cells collected from the test animal is measured, and the obtained measurement value is less than a predetermined reference value, it is evaluated that heart failure of the test animal is highly likely to be severe, and if the measurement value is equal to or larger than the reference value, it is evaluated that heart failure of the test animal is highly likely to be mild.

[4] The method of evaluating pathological conditions of heart failure according to [1], wherein, when the test animal is confirmed to have heart failure and the respiratory capacity of mitochondrial complex II in peripheral blood mononuclear cells collected from the test animal is measured, and the obtained measurement value is lower than a measurement value of the respiratory capacity of mitochondrial complex II in peripheral blood mononuclear cells collected from the test animal before the peripheral blood mononuclear cells are collected, it is evaluated that heart failure of the test animal is highly likely to be severe.

[5] The method of evaluating pathological conditions of heart failure according to [1], wherein, when the test animal is confirmed to have heart failure, and an amount of reactive oxygen species released from peripheral blood mononuclear cells collected from the test animal is measured, and the obtained measurement value is larger than a predetermined reference value, it is evaluated that heart failure of the test animal is highly likely to be severe, and if the measurement value is equal to or less than the reference value, it is evaluated that heart failure of the test animal is highly likely to be mild.

[6] The method of evaluating pathological conditions of heart failure according to [1], wherein, when the test animal is confirmed to have heart failure, and an amount of reactive oxygen species released from peripheral blood mononuclear cells collected from the test animal is measured, and the obtained measurement value is larger than a measurement value of the amount of reactive oxygen species released from peripheral blood mononuclear cells collected from the test animal before the peripheral blood mononuclear cells are collected, it is evaluated that heart failure of the test animal is highly likely to be severe.

[7] The method of evaluating pathological conditions of heart failure according to any one of [1] to [6], wherein the heart failure is chronic heart failure.

[8] A biomarker for which an amount of succinyl-CoA in cardiomyocytes is used and used for evaluating the onset of heart failure or the severity of heart failure.

[9] A biomarker for which a respiratory capacity of mitochondrial complex II in peripheral blood mononuclear cells or an amount of reactive oxygen species released from peripheral blood mononuclear cells is used and used for evaluating the onset of heart failure or the severity of heart failure.

[10] A method of evaluating a candidate compound for a heart failure treatment drug, including: bringing a candidate compound into contact with cells and measuring an amount of succinyl-CoA in the cells; and evaluating usefulness of the candidate compound as a heart failure treatment drug based on the obtained measurement value.

[11] The method of evaluating a candidate compound for a heart failure treatment drug according to [10], wherein the cells are myocardium-derived cultured cells.

[12] The method of evaluating a candidate compound for a heart failure treatment drug according to [10] or [11], wherein the cells are cells treated with glycine in advance.

[13] A method of evaluating a candidate compound for a heart failure treatment drug, including: bringing a candidate compound into contact with cells and measuring a respiratory capacity of mitochondrial complex II in the cells or an amount of reactive oxygen species released from the cells; and evaluating usefulness of the candidate compound as a heart failure treatment drug based on the obtained measurement value.

[14] A pharmaceutical composition including a compound having an action of increasing the amount of succinyl-CoA in cardiomyocytes as an active component and used for treatment or prevention of heart failure.

[15] The pharmaceutical composition according to [14], wherein the compound is succinyl-CoA, 5-aminolevulinic acid, 5-aminolevulinic acid derivatives, or pharmaceutically acceptable salts thereof.

[16] A heart failure treatment method, including increasing an amount of succinyl-CoA in cardiomyocytes for an animal with heart failure.

[17] The heart failure treatment method according to [16], wherein succinyl-CoA, 5-aminolevulinic acid, 5-aminolevulinic acid derivatives, or pharmaceutically acceptable salts thereof are administered to the animal.

Advantageous Effects of Invention

According to the method of evaluating pathological conditions of heart failure of the present invention, it is possible to evaluate the onset of heart failure in test animals and the severity of heart failure. In addition, the pharmaceutical composition according to the present invention is useful for treatment or prevention of heart failure.

DESCRIPTION OF EMBODIMENTS

Figure 1:
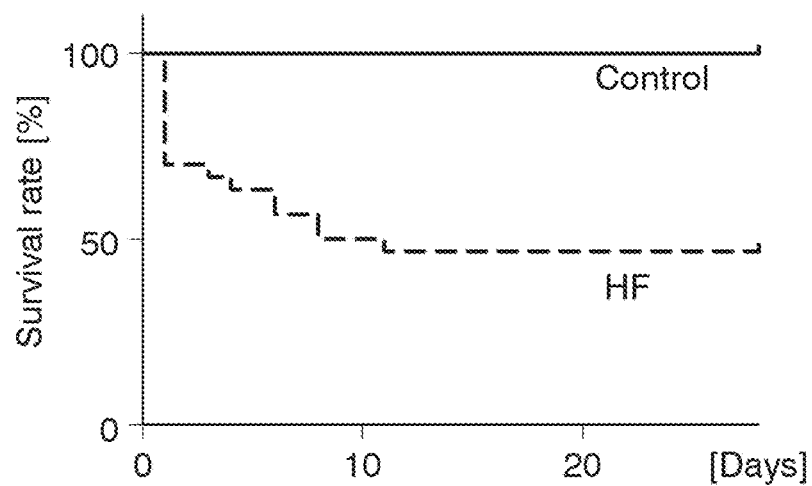
FIG. 1 is a diagram showing survival curves of HF model mice and control mice in Reference Example 1.

<Method of Evaluating Pathological Conditions of Heart Failure and Biomarker>

In heart failure, the amount of succinyl-CoA is reduced and consequently functions of mitochondrial complex II deteriorate. That is, in animals with heart failure, the amount of succinyl-CoA in cardiomyocytes is lower than before the onset of heart failure. In addition, when pathological conditions of heart failure become more severe, functions of mitochondrial complex II greatly deteriorate, and the amount of succinyl-CoA in cardiomyocytes is also reduced. Therefore, the amount of succinyl-CoA in cardiomyocytes is useful as a biomarker that is used to evaluate pathological conditions of heart failure, specifically, the onset of heart failure or a likelihood thereof, and the severity of heart failure or a likelihood thereof, and it is possible to evaluate pathological conditions of heart failure based on this. The evaluation method is particularly suitable for evaluating chronic heart failure.

Specifically, the method of evaluating pathological conditions of heart failure according to the present invention is a method including measuring an amount of succinyl-CoA in cardiomyocytes collected from test animals and evaluating the onset of heart failure of the test animals or the severity of heart failure based on the obtained measurement value. For example, when it is unknown whether a test animal has heart failure and the measurement value of the amount of succinyl-CoA in cardiomyocytes collected from the animal is less than a predetermined reference value set in advance, it is possible to evaluate that the test animal has a high likelihood of the onset of heart failure.

On the other hand, if the measurement value of the amount of succinyl-CoA in cardiomyocytes is a predetermined reference value set in advance or larger, it is possible to evaluate that the test animal has a low likelihood of the onset of heart failure. In addition, when the test animal is an animal that has been confirmed to have heart failure, and the measurement value of the amount of succinyl-CoA in cardiomyocytes collected from the animal is less than a predetermined reference value set in advance, it is possible to evaluate that heart failure of the test animal is highly likely to be severe. On the other hand, if the measurement value of the amount of succinyl-CoA in cardiomyocytes is a predetermined reference value set in advance or larger, it is possible to evaluate that heart failure of the test animal is unlikely to be severe or highly likely to be mild.

The reference value used when the measurement value of the amount of succinyl-CoA in cardiomyocytes is evaluated can be appropriately set in consideration of the type of method of measuring the amount of succinyl-CoA and the like or by performing a required preliminary examination and the like. For example, based on the results of other examination methods, a threshold value for distinguishing between the group with heart failure and the group without heart failure can be appropriately set by comparing the measurement value of the amount of succinyl-CoA in cardiomyocytes collected from test animals confirmed not to have heart failure with the measurement value of the amount of succinyl-CoA in cardiomyocytes collected from test animals confirmed to have heart failure, and this can be used as a reference value.

The method of measuring the amount of succinyl-CoA in cardiomyocytes is not particularly limited as long as it is possible to measure an organic compound in cells quantitatively or semi-quantitatively, and it can be appropriately selected from among known methods used for detecting an organic compound in a specimen and used. Each method can be performed by a conventional method. For example, first, the myocardium collected from a test animal is homogenized in a polar solvent, for example, a mixed solvent containing an alcohol and water, and various organic compounds including succinyl-CoA are extracted. The obtained extract is separated into succinyl-CoA and other organic compounds by high performance liquid chromatography (HPLC). Based on the peak area value of the peak of succinyl-CoA in the obtained chromatograph, the amount of succinyl-CoA can be measured by a conventional method.

In addition, mitochondrial dysfunction and oxidative stress play important roles in the onset of heart failure. In animals with heart failure, particularly, with chronic heart failure, the respiratory capacity of mitochondrial complex II in PBMC and the amount of ROS released from PBMC change depending on the severity of heart failure. Specifically, when the severity of heart failure is higher, the respiratory capacity of mitochondrial complex II in PBMC tends to be lower and the amount of ROS released from PBMC tends to be larger. In addition, in animals with heart failure, the respiratory capacity of mitochondrial complex II in PBMC tends to decrease and the amount of ROS released from PBMC tends to increase compared with before the onset of heart failure. Therefore, the respiratory capacity of mitochondrial complex II in PBMC and the amount of ROS released from PBMC are useful as biomarkers that are used to evaluate pathological conditions of heart failure, specifically, the onset of heart failure, or a likelihood thereof, and the severity of heart failure or a likelihood thereof, and it is possible to evaluate pathological conditions of heart failure based on this. The evaluation method is particularly suitable for evaluating chronic heart failure.

Specifically, the method of evaluating pathological conditions of heart failure according to the present invention also includes a method including measuring a respiratory capacity of mitochondrial complex II in PBMC collected from a test animal or an amount of ROS released from PBMC and evaluating the onset of heart failure of the test animal or the severity of heart failure based on the obtained measurement value. It is possible to evaluate the obtained measurement value based on a predetermined reference value set in advance.

For example, when it is unknown whether a test animal has heart failure and the measurement value of the respiratory capacity of mitochondrial complex II in PBMC collected from the animal is less than a predetermined reference value set in advance, it is possible to evaluate that the test animal has a high likelihood of the onset of heart failure. On the other hand, when the measurement value of the respiratory capacity of mitochondrial complex II in PBMC is a predetermined reference value set in advance or larger, it is possible to evaluate that the test animal has a low likelihood of the onset of heart failure. In addition, when the test animal is an animal that has been confirmed to have heart failure and the measurement value of the respiratory capacity of mitochondrial complex II in PBMC collected from the animal is less than a predetermined reference value set in advance, it is possible to evaluate that heart failure of the test animal is highly likely to be severe. On the other hand, when the measurement value of the respiratory capacity of mitochondrial complex II in PBMC is a predetermined reference value set in advance or larger, it is possible to evaluate that heart failure of the test animal is unlikely to be severe or highly likely to be mild.

For example, when it is unknown whether a test animal has heart failure and the measurement value of the amount of ROS released from PBMC collected from the animal is larger than a predetermined reference value set in advance, it is possible to evaluate that the test animal has a high likelihood of the onset of heart failure. On the other hand, when the measurement value of the amount of ROS released from PBMC is a predetermined reference value set in advance or less, it is possible to evaluate that the test animal has a low likelihood of the onset of heart failure. In addition, when the test animal is an animal that has been confirmed to have heart failure and the measurement value of the amount of ROS released from PBMC collected from the animal is larger than a predetermined reference value set in advance, it is possible to evaluate that heart failure of the test animal is highly likely to be severe. On the other hand, when the measurement value of the amount of ROS released from PBMC is a predetermined reference value set in advance or less, it is possible to evaluate that heart failure of the test animal is unlikely to be severe or highly likely to be mild.

In addition, for test animals confirmed to have heart failure, the respiratory capacity of mitochondrial complex II in PBMC or the amount of ROS released from PBMC are measured over time, and thus it is possible to evaluate the severe of heart failure. Specifically, when the measurement value of the respiratory capacity of mitochondrial complex II in PBMC collected from the test animal is lower than the measurement value of the respiratory capacity of mitochondrial complex II in PBMC collected before the PBMCs are collected from the same test animal, it is evaluated that heart failure of the test animal is highly likely to be severe. Similarly, when the measurement value of the amount of ROS released from PBMC collected from the test animal is larger than the measurement value of the amount of ROS released from PBMC collected before the PBMCs are collected from the same test animal, it is possible to evaluate that heart failure of the test animal is highly likely to be severe.

The reference value used when the measurement value of the respiratory capacity of mitochondrial complex II in PBMC is evaluated can be appropriately set in consideration of the type of method of measuring the respiratory capacity of mitochondrial complex II and the like or by performing a required preliminary examination and the like. Similarly, the reference value used when the measurement value of the amount of ROS released from PBMC is evaluated can be appropriately set in consideration of the type of method of measuring the amount of ROS or by performing a required preliminary examination and the like. For example, based on the results of other examination methods, a threshold value for distinguishing between the group with heart failure and the group without heart failure can be appropriately set by comparing the measurement value of the respiratory capacity of mitochondrial complex II in PBMC collected from test animals confirmed not to have heart failure or the amount of ROS released from PBMC with the measurement value of the respiratory capacity of mitochondrial complex II in PBMC collected from test animals confirmed to have heart failure or the amount of ROS released from PBMC, and this can be used as a reference value. Similarly, based on the results of other examination methods, a threshold value for distinguishing between a mild heart failure group and a severe heart failure group can be appropriately set by comparing the measurement value of the respiratory capacity of mitochondrial complex II in PBMC collected from test animals confirmed to have heart failure that is not severe, that is, to have mild heart failure, or the amount of ROS released from PBMC, with the measurement value of the respiratory capacity of mitochondrial complex II in PBMC collected from test animals confirmed to have severe heart failure or the amount of ROS released from PBMC, and this can be used as a reference value.

Collection of PBMC from test animals can be performed in sampled blood by a conventional method such as a density gradient centrifugation method. The respiratory capacity of mitochondrial complex II in the collected PBMC can be measured by a conventional method such as a high-resolution respiration measurement method. A device such as a mitochondrial oxygen activity/cell metabolic energy analyzing device is preferably used to measure the respiratory capacity of mitochondrial complex II in PBMC according to a high-resolution respiration measurement method. In addition, the amount of ROS released from PBMC can be measured by a conventional method such as fluorescence spectroscopy.

Test target animals in which the amount of succinyl-CoA in cardiomyocytes, the respiratory capacity of mitochondrial complex II in PBMC, or the amount of ROS released from PBMC is used as a diagnostic marker for evaluating pathological conditions of heart failure are not particularly limited, and may be humans or non-human animals. Examples of non-human animals include mammals such as cows, pigs, horses, sheep, goats, monkeys, dogs, cats, rabbits, mice, rats, hamsters, and guinea pigs, and birds such as chickens, quails, and ducks.

<Pharmaceutical Composition and Heart Failure Treatment Method>

In heart failure, when the amount of succinyl-CoA in cardiomyocytes is increased, functions of mitochondrial complex II are improved, and pathological conditions of heart failure are improved. That is, the heart failure treatment method according to the present invention is a method of increasing the amount of succinyl-CoA in cardiomyocytes for animals with heart failure. For example, when an effective amount of a compound having an action of increasing the amount of succinyl-CoA in cardiomyocytes is administered to an animal with heart failure, it is possible to improve pathological conditions of heart failure of the animal. In addition, when an effective amount of a compound having an action of increasing the amount of succinyl-CoA in cardiomyocytes is administered to an animal having a likelihood of heart failure, it is possible to prevent the animal from developing heart failure.

The compound having an action of increasing the amount of succinyl-CoA in cardiomyocytes is useful as an active component of a pharmaceutical composition used for treatment or prevention of heart failure. For the compound, when the amount of succinyl-CoA in the cells before administration is set as 100%, a compound that can increase the amount of succinyl-CoA in cardiomyocytes to 110% or more is preferable, a compound that can increase the amount of succinyl-CoA in cardiomyocytes to 120% or more is more preferable, and a compound that can increase the amount of succinyl-CoA in cardiomyocytes to 150% or more is still more preferable.

Examples of compounds having an action of increasing the amount of succinyl-CoA in cardiomyocytes include succinyl-CoA, 5-aminolevulinic acid (ALA). ALA derivatives, and pharmaceutically acceptable salts thereof. Regarding pharmaceutically acceptable salts of ALA. ALA derivatives, and pharmaceutically acceptable salts of ALA derivatives, for example, those described in PCT International Publication No. WO 2010/050179 can be used.

A route of administration of a pharmaceutical composition which includes a compound having an action of increasing the amount of succinyl-CoA in cardiomyocytes as an active component and is used for treatment or prevention of heart failure (hereinafter referred to as a "pharmaceutical composition for heart failure treatment" in some cases) is not particularly limited. Examples of routes of administration of the pharmaceutical composition include oral administration, transdermal administration, nasal administration, intravenous administration, intraperitoneal administration, and enema administration.

The pharmaceutical composition for heart failure treatment can be formulated into solid preparations such as powders, granules, capsules, tablets, chewable agents, and sustained-release tablets, liquid agents such as solution agents and syrups, injection agents, spray agents, patch agents, ointments, or the like by general methods. The pharmaceutical composition is preferably a solid preparation that can be orally administered.

The pharmaceutical composition for heart failure treatment is formulated by adding an excipient, a binder, a lubricant, a disintegrant, a fluidizing agent, a solvent, a solubilizing agent, a buffer, a suspension agent, an emulsifier, an isotonizing agent, a stabilizer, a preservative, an anti-oxidizing agent, a flavoring agent, a coloring agent as necessary for formulation to a compound having an action of increasing the amount of succinyl-CoA in cardiomyocytes as an active component.

Examples of excipients include sugars such as lactose, glucose, and d-mannitol, celluloses such as starch and crystalline cellulose, sugar alcohols such as erythritol, sorbitol, and xylitol, and dicalcium phosphate, calcium carbonate, and kaolin. Examples of binders include pregelatinized starch, gelatin, gum arabic, methyl cellulose, carboxymethyl cellulose, sodium carboxymethyl cellulose, crystalline cellulose, d-mannitol, trehalose, hydroxypropyl cellulose, hydroxypropyl methyl cellulose, polyvinylpyrrolidone, and polyvinyl alcohol. Examples of lubricants include stearic acid, calcium stearate, talc, sucrose fatty acid ester, and polyethylene glycol. Examples of disintegrants include crospovidone (crosslinked polyvinylpyrrolidone), low substituted hydroxypropylcellulose, starch, alginic acid, and sodium alginate. Examples of fluidizing agents include silicic acid, silicon dioxide, aluminum silicate, calcium silicate, magnesium aluminate metasilicate compounds, aluminum oxide, aluminum hydroxide, magnesium oxide, and magnesium hydroxide. Examples of solvents include purified water and salines. Examples of solubilizing agents include dextran, polyvinylpyrrolidone, sodium benzoate, ethylenediamine, salicylic acid amide, nicotinamide, and polyoxyethylene hydrogenated castor oil derivatives. Examples of buffers include sodium citrate hydrate, sodium acetate hydrate, sodium bicarbonate, trometamol, boric acid, borax, sodium hydrogen phosphate hydrate, and sodium dihydrogen phosphate. Examples of suspension agents or emulsifiers include sodium lauryl sulfate, gum arabic, gelatin, lecithin, glycerin monostearate, polyvinyl alcohols, polyvinylpyrrolidone, celluloses such as sodium carboxymethyl cellulose, polysorbates, and polyoxyethylene hydrogenated castor oils. Examples of isotonizing agents include sugars such as lactose, glucose, and d-mannitol, sodium chloride, potassium chloride, glycerin, propylene glycol, polyethylene glycol, and urea. Examples of stabilizers include polyethylene glycol, dextran sodium sulfate, and sodium sulfite. Examples of preservatives include paraoxybenzoic acid esters, chlorobutanol, benzyl alcohol, phenethyl alcohol, chlorocresol, dehydroacetic acid, and sorbic acid. Examples of anti-oxidizing agents include sulfites and ascorbic acid. Examples of flavoring agents include sweeteners and fragrance materials commonly used in the pharmaceutical and food fields. Examples of coloring agents include coloring agents commonly used in the pharmaceutical and food fields.

The pharmaceutical composition may contain other active components as long as it does not impair an action of increasing the amount of succinyl-CoA for cardiomyocytes. Examples of other active components include substances expected to have a heart failure treatment effect such as a heart failure treatment agent that targets a marker other than the amount of succinyl-CoA for cardiomyocytes.

Test target animals for which heart failure is treated or prevented using a pharmaceutical composition for heart failure treatment are not particularly limited, and may be humans or non-human animals. Examples of non-human animals include the same animals exemplified above.

The dose of the pharmaceutical composition for heart failure treatment (including the formulation thereof) may be an amount sufficient to increase the amount of succinyl-CoA in cardiomyocytes of an animal to which the composition is administered compared with that before administration, and varies depending on the species, gender, age, body weight, and diet of administration subjects, the mode of administration, other diseases, and the like. For example, a daily dose of the pharmaceutical composition for heart failure treatment for adults (with a body weight of 60 kg) is preferably 0.01 to 5,000 mg, more preferably 0.1 to 3,000 mg, and still more preferably 1 to 1,000 mg of the compound having an action of increasing the amount of succinyl-CoA in cardiomyocytes as an active component. Such a dose can be administered once or a plurality of times.

<Method of Evaluating Candidate Compound for Heart Failure Treatment Drug>

It is possible to screen an active component of a drug used for treatment or prevention of heart failure (heart failure treatment drug) using an increase in the amount of succinyl-CoA in cells, an increase in the respiratory capacity of mitochondrial complex II in cells or a decrease in the amount of ROS released from cells as an indicator. That is, the method of evaluating a candidate compound for a heart failure treatment drug according to the present invention is a method in which a candidate compound is brought into contact with cells, the amount of succinyl-CoA in the cells, the respiratory capacity of mitochondrial complex II in the cells, or the amount of ROS released from the cells is measured, and based on the obtained measurement value, the usefulness of the candidate compound as a heart failure treatment drug is evaluated. The amount of succinyl-CoA in cells, the respiratory capacity of mitochondrial complex II in cells, or the amount of ROS released from cells can be measured in the same manner as in the measurement of the amount of succinyl-CoA in cardiomyocytes collected from the animal, the respiratory capacity of mitochondrial complex II in cells or the amount of ROS released from cells.

Cells used in the evaluation method may be primary subcultured cells, but in consideration of stability of the evaluation method, cultured cells are preferable. When the increase in the amount of succinyl-CoA in cells is used as an indicator, the cultured cells are preferably myocardium-derived cultured cells, more preferably mammal myocardium-derived cultured cells, and still more preferably human myocardium-derived cultured cells. When the increase in the respiratory capacity of mitochondrial complex II in cells or the decrease in the amount of ROS released from cells is used as an indicator, the cultured cells are preferably cultured cells derived from hematopoietic cells including PBMC, more preferably cultured cells derived from hematopoietic cells of mammals, and still more preferably cultured cells derived from hematopoietic cells of humans.

When the increase in the amount of succinyl-CoA in cells is used as an indicator, the cells used in the evaluation method are preferably cells in which functions of mitochondrial complex ii deteriorate. Examples of cells in which functions of mitochondrial complex II deteriorate include cells in which cells used for evaluation are treated with glycine in advance. According to the glycine treatment, as in heart failure, the succinylation level of mitochondria is lowered, and the respiratory capacity related to mitochondrial complex II decreases. The glycine treatment can be performed by performing culturing in a culture medium containing glycine.

In the evaluation method, a method of bringing a candidate compound into contact with cells is not particularly limited. For example, when a candidate compound is added to a cell culture medium, the candidate compound can be brought into contact with cells.

When the increase in the amount of succinyl-CoA in cells is used as an indicator, if the measurement value of the amount of succinyl-CoA in cells treated with a candidate compound is a predetermined reference value set in advance or larger, it is possible to evaluate that the candidate compound is useful as an active component of the heart failure treatment drug. On the other hand, if the measurement value of the amount of succinyl-CoA in cells treated with a candidate compound is less than a predetermined reference value set in advance, it is possible to evaluate that the candidate compound is not useful as an active component of the heart failure treatment drug.

When the increase in the amount of succinyl-CoA in cells is used as an indicator, the reference value used when a candidate compound is evaluated in the candidate compound evaluation method can be appropriately set in consideration of the type of method of measuring the amount of succinyl-CoA, the type of cells to be used, and the like or by performing a required preliminary examination and the like. For example, based on the results of other examination methods, a threshold value for distinguishing between a cell group treated with a compound and a cell group not treated with the compound can be appropriately set by comparing the measurement value of the amount of succinyl-CoA in cells treated with the compound confirmed to have an action of increasing the amount of succinyl-CoA in cells with the measurement value of the amount of succinyl-CoA in cells before treatment with the compound, and this can be used as a reference value. Examples of compounds confirmed to have an action of increasing the amount of succinyl-CoA in cells include succinyl-CoA, ALA, ALA derivatives, and pharmaceutically acceptable salts thereof.

When the increase in the respiratory capacity of mitochondrial complex II in cells is used as an indicator, if the measurement value of the respiratory capacity of mitochondrial complex II in cells treated with a candidate compound is a predetermined reference value set in advance or larger, it is possible to evaluate that the candidate compound is useful as an active component of the heart failure treatment drug. On the other hand, if the measurement value of the respiratory capacity of mitochondrial complex II in cells treated with a candidate compound is less than a predetermined reference value set in advance, it is possible to evaluate that the candidate compound is not useful as an active component of the heart failure treatment drug.

When the decrease in the amount of ROS released from cells is used as an indicator, if the measurement value of the amount of ROS released from cells treated with a candidate compound is a predetermined reference value set in advance or less, it is possible to evaluate that the candidate compound is useful as an active component of the heart failure treatment drug. On the other hand, if the measurement value of the amount of ROS released from cells treated with a candidate compound is larger than a predetermined reference value set in advance, it is possible to evaluate that the candidate compound is not useful as an active component of the heart failure treatment drug.

When the increase in the respiratory capacity of mitochondrial complex II in cells is used as an indicator, the reference value used when a candidate compound is evaluated in the candidate compound evaluation method can be appropriately set in consideration of the type of method of measuring the respiratory capacity of mitochondrial complex II and the like or by performing a required preliminary examination and the like. For example, based on the results of other examination methods, a threshold value for distinguishing between a cell group treated with a compound and a cell group not treated with the compound can be appropriately set by comparing the measurement value of the respiratory capacity of mitochondrial complex II in cells treated with the compound confirmed to have an action of increasing the respiratory capacity of mitochondrial complex II in cells with the measurement value of the respiratory capacity of mitochondrial complex II in cells before treatment of the compound, and this can be used as a reference value.

When the decrease in the amount of ROS released from cells is used as an indicator, the reference value used when a candidate compound is evaluated in the candidate compound evaluation method can be appropriately set in consideration of the type of the method of measuring the amount of ROS and the like or by performing a required preliminary examination and the like. For example, based on the results of other examination methods, a threshold value for distinguishing between a cell group treated with a compound and a cell group not treated with the compound can be appropriately set by comparing the measurement value of the amount of ROS in cells treated with the compound confirmed to have an action of decreasing the amount of ROS in cells with the measurement value of the amount of ROS in cells before treatment with the compound, and this can be used as a reference value.

EXAMPLES

Next, while the present invention will be described in more detail with reference to examples and the like, the present invention is not limited to the following examples.
<Echocardiography>

Echocardiography was performed under anesthesia (Avastin 8 µL/gBW, intraperitoneal administration) with a short duration of action and least impact on the cardiovascular system. The limbs and tail were fixed in a lying position to an examination table with a tape and the anterior chest wall of the mice was depilated with a depilatory cream. Using an ultrasonic diagnostic device and a 12 MHz linear probe, optimal 2D parasternal short-axis images were visualized at the papillary muscle level. Switching to an M mode method was performed, recording was performed at a recording paper speed of 40 mm/s, and a heart rate, a left ventricular end-diastolic dimension, a left ventricular end-systolic dimension, a left ventricular anterior wall thickness, a left ventricular posterior wall thickness, and a left ventricular fractional shortening were measured.

<Mitochondrial Isolation>

Mitochondrial isolation from mice was performed as follows.

First, the heart (left ventricle) extracted from euthanized mice under anesthesia was immersed in a tissue preservation solution BIOPS (2.77 mM $CaK_2EGTA$, 7.23 mM $K_2EGTA$, 5.77 mM $Na_2ATP$, 6.56 mM $MgCl_2/6H_2O$, 20 mM taurine, 15 mM $Na_2$ phosphocreatine, 20 mM imidazole, 0.5 mM dithiothreitol, 50 mM MES hydrate, pH 7.1), and then shredded in a tissue isolation buffer (100 mM sucrose, 100 mM KCl, 50 mM tris-HCl, 1 mM $KH_2PO_4$, 0.1 mM EGTA, 0.2% bovine serum albumin, pH 7.4). Protease was added to this shredded product to cause an enzyme reaction and homogenization was then performed. The obtained homogenized solution was centrifuged to remove the supernatant, and the precipitate was washed with a tissue isolation buffer twice. A suspension buffer (225 mM mannitol, 75 mM sucrose, 10 mM tris-HCl, 0.1 mM EDTA, pH 7.4) was added to the washed precipitate and the precipitate was dissolved.

<Measurement of Concentration of Mitochondrial Proteins>

The protein concentration of the isolated mitochondria was measured using a BCA protein assay kit (commercially available from Pierce). A calibration curve was created using albumin as a standard substance. The protein concentration was measured for n=2, and the average value of two measurement values was used.

<Cell Membrane Permeation Treatment of Myocardial Fibrous Tissues>

The cell membrane permeation treatment of myocardial fibrous tissues collected from mice was performed as follows.

The myocardium removed from the euthanized mice was immediately immersed in an ice-cooled BIOPS and the surrounding tissues were then removed as much as possible in the BIOPS. Next, the cell membrane permeation treatment was performed by loosening myocardial fibers in the BIOPS with two 18-gauge injection needles and then vibrating in a BIOPS solution containing saponin (surfactant) for 30 minutes. Myocardial fibers after the cell membrane permeation treatment were immersed in a MiR05 buffer (0.5 mM EGTA, 3 mM $MgCl_2$, 20 mM taurine, 10 mM $KH_2PO_4$, 20 mM HEPES, 110 mM sucrose, 60 mM potassium lactobionate, 1 g/L BSA) for 10 minutes and a washing treatment was then performed twice in order to remove the supernatant.

<Measurement of Mitochondrial Respiratory Capacity>

A mitochondrial respiratory capacity (oxidative phosphorylation: OXPHOS) was measured by a high-resolution respiration measurement method. Specifically, isolated mitochondria (50 to 100 µg) or myocardial fibrous tissues (0.5 to 3 mg) after the cell membrane permeation treatment were used as a test sample, and measurement was performed using a mitochondrial oxygen activity/cell metabolic energy analyzing device (product name: "OROBOROS Oxygraph-2 k," commercially available from Innsbruck) (hereinafter referred to as a "mitochondrial respiratory capacity measurement device" in some cases) under an environment at 37° C. according to the following protocol. An oxygen consumption amount was calculated using Datlab software, and in this case, correction was performed per tissue weight or per mitochondrion.

(1) A 2 mL chamber was filled with an MiR05 buffer and covered with a lid and air was expelled. Next, the test sample was put into the chamber, and 3 mmol/L of magnesium chloride and 10 mmol/L of ADP were additionally added.

(2) 10 mmol/L of glutamic acid, 2 mmol/L of malic acid, and 5 mmol/L of pyruvic acid, which are substrates related to mitochondrial complex I, were added, and the oxygen consumption amount was measured (CI_OXPHOS).

(3) 10 mmol/L of succinic acid, which is a substrate related to mitochondrial complex II, was added, and the oxygen consumption amount was measured (CI+II_OXPHOS).

(4) In order to observe the respiration of OXPHOS of mitochondrial complex II alone, 0.5 μmol/L of rotenone, which is an inhibitor of mitochondrial complex I, was added and the oxygen consumption amount was measured (CII_OXPHOS).

(5) In order to observe the ADP-independent leaked respiration, 2.5 μmol/L of oligomycin, which is an inhibitor of ATPase, was added and the oxygen consumption amount was measured (CII_LEAK).

(6) In order to observe a maximum respiration function, 1 μmol/L of FCCP (carbonyl cyanide-p-trifluoromethoxyphenylhydrazone), which is an uncoupling agent, was added, and oxygen consumption amount was measured (CII_ETS).

(7) 2.5 μmol/L of Antimycin A, which is an inhibitor of mitochondrial complex II, was added, and respiration related to mitochondria was stopped (ROX).

(8) The respiratory capacity when 2 mmol/L of ascorbic acid and 0.5 mmol/L of TMPD (N,N,N',N'-tetramethyl-p-phenylenediamine), which are substrates of mitochondrial complex IV, were added was measured. Next, the respiratory capacity when 100 mmol/L of sodium azide as an inhibitor was added was measured, and a difference therebetween was calculated (CIV_OXPHOS).

<Analysis of Metabolite from Myocardium by Liquid Chromatography Mass Spectrometry>

Analysis of metabolite of myocardial fibrous tissues collected from mice was performed as follows.

First, myocardial tissues (70 to 90 mg) frozen with liquid nitrogen were crushed with small metal pieces using a MultiBeads Shocker at 2,000 rpm for 10 seconds. A dissolution buffer (70% methanol, 10 mg/mL MES (2-(N-Morpholino)-ethanesulfonic acid)) was mixed with the crushed sample and dissolving was performed using an ultrasonic crushing process (5 sets of ultrasonic treatment for 30 seconds and then cooling for 30 seconds were repeated). 21,500 g of the obtained dissolved material was centrifuged for 5 minutes, and the supernatant was collected and used as a sample for liquid chromatography mass spectrometry (LC-MS).

A 5 μL LC-MS sample was applied to an ACQUITY BEH column (commercially available from Waters) and separated, and analyzed using a high performance liquid chromatography-triple quadrupole mass spectrometry (LCMS-8040, commercially available from Shimadzu Corporation). A moving phase was an eluent A (15 mM acetic acid, 10 mM tributylamine, 3% methanol) and an eluent B (100% methanol). Gradient elution gradually increased the proportion of the eluent B as follows: the concentration of the eluent B was 0% for 0 to 6 minutes, the concentration of the eluent B linearly increased from 0% to 90% for 6 to 26 minutes, and the concentration of the eluent B then decreased to 0% for 26 to 41 minutes. The flow velocity was 0.3 mL/min, the column oven temperature was 40° C., and parameters related to electrospray ionization were as follows: the drying gas flow velocity was 15 L/min; the nebulizer gas flow velocity was 3 L/min; the heating gas was 10 L/min; the desolvation line temperature was 250° C.; the heat block temperature was 400° C.; and the collision gas was 230 kPa. Labsolutions software (commercially available from Shimadzu Corporation) was used for data analysis, and an MES signal was used as a standard for signal intensity.

<Measurement of Ketone Bodies (β-OHB)>

(i-OHB in the myocardium was measured using a beta HB Assay kit (ab83390. commercially available from Abcam).

Specifically, myocardium (15 to 20 mg) collected from the mice and a 200 μL beta HB Assay Buffer were put into a glass homogenizer, homogenized 15 times, centrifugation was then performed at 20,000 g for 5 minutes, and the supernatant was collected. 20 μL of 6 M perchloric acid (PCA) was added to 100 μL of the collected supernatant and incubation was performed on ice for 5 minutes, centrifugation was then performed at 13,000 g for 2 minutes, and the supernatant was collected. 2 M KOH was added to the collected supernatant so that the pH was 6.5 to 8.0, centrifugation was then performed at 13.000 g for 15 minutes, and the supernatant was collected. The collected supernatant was used as a measurement sample.

A 50 μL measurement sample and 50 μL Reaction Mix (a mixed solution containing 46 μL of beta HB Assay Buffer, 2 μL of Enzyme Mix, and 2 μL of Substrate Mix) were added to a 96-well plate well, light was blocked, incubation was performed at room temperature for 30 minutes, and the absorbance at a wavelength of 450 nm was then measured with a microplate reader. Based on the calibration curve obtained from the standard absorbance attached to the kit, the amount of J-OHB of the sample was calculated from the measured absorbance.

<Measurement of Mitochondrial Heme>

The mitochondrial heme in the myocardium was measured using QuantiChrom (registered trademark) Heme Assay Kit (DIHM-250, commercially available from BioAssay Systems).

Specifically, first, mitochondria were isolated from the myocardium collected from the mice to prepare a sample solution with a protein concentration of 100 μg/50 μL.

Next, a 50 μL sample solution and a 200 μL Reagent were added to a 96-well plate well, and the absorbance with a wavelength of 400 nm was measured with a microplate reader. For a control, the absorbance was measured in the same manner using Calibrator attached to the kit. The heme concentration of the control was 62.5 μM. and the mitochondrial heme concentration of the sample was calculated based on the measurement value of the absorbance.

<Succinylation Assay of Mitochondrial Proteins>

The succinylation assay of intochondrial proteins was performed as follows.

Succinyl-CoA (0, 0.3, 1, 3, or 10 mM) was added to the mitochondria isolated from tissues or cells, and the mixture was left at 30° C. for 15 minutes. Then, the succinylation level of the mitochondrial proteins was measured by western blotting (WB).

<Desuccinylation Assay of Mitochondrial Proteins>

The desuccinylation assay of mitochondrial proteins was performed by adding proteins to be succinylated and measuring the succinylation level of the proteins. The succinylation level of the proteins was measured by LC/MS/MS.

When lysine was used, lysine (1.0 or 10 mM) was added to the mitochondria isolated from mouse myocardium, and incubation was performed for 15 minutes. In consideration of an effect of pH change due to addition of lysine, the pH was adjusted by adding HCl. Then, the succinylation level of the mitochondrial proteins was measured by WB.

When STRT5 was used, recombinant SIRT5 (20 μg) and NAD (5 mM) were added to the mitochondria isolated from mouse myocardium, succinyl-CoA (0, 3, or 10 mM) was additionally added, and the mixture was left at 37° C. for 60 minutes. Then, the succinylation level of the mitochondrial proteins was measured by WB.

When glycine was used, glycine was added to the culture medium for cultured H9c2 cells so that the concentration was 100 mM, and the cells were cultured for 6 hours. After culturing, the cells were collected and mitochondria were isolated. Then, the succinylation level of the mitochondrial proteins was measured by WB.

<Statistical Analysis>

Statistical processing was performed using GraphPad Prism 7 software (commercially available from Graphpad Software). Data is shown as average value±standard error. The difference of average values between two groups was tested by Student's T test. The difference of average values between many groups was tested using one-way analysis of variance, and when a significant difference was found, a multiple comparison test was performed by the Tukey method or the Dunnett method. A P value<0.05 was determined to be statistically significant.

Here, in the drawings, values marked with an asterisk indicate that they are statistically significant.

[Reference Example 1] Preparation of Heart Failure (HF) Model Mice

The HF model mice to be used in subsequent experiments were prepared as follows.

The left anterior descending coronary artery of the heart of 10- to 12-week old male C57BL/6J mice (body weight of 23 to 26 g) was ligated to cause myocardial infarction (MI). The body weight of the mice was measured before the operation, a mixed anesthetic containing 3 types including 0.3 mg/kg BW of medetomedine hydrochloride, 4.0 mg/kg BW of midazolam, and 5.0 mg/kg BW of butorphanol tartrate was intraperitoneally administered, and it was confirmed that the depth of anesthesia was sufficient. The limbs and tail of the mice were fixed in a lying position to an operating table with a tape, and incisors were pulled with a silk thread and the neck was fixed in the extended portion for tracheal intubation. After midline skin incision of the neck, the submandibular gland and anterior tracheal muscle were expanded, and it was confirmed in a direct-view that a 23-gauge polyethylene tube passed through the translucent tracheal cartilage while maintaining the linear shape of the trachea. Then, it was connected to a volume-controlled experiment animal ventilator, artificial respiration with 110 times for each time and with a tidal volume of 0.4 mL started, and it was confirmed that the precordium was well lifted during insufflation.

Disinfection was performed with a 70% alcohol, and the operation was performed under a stereomicroscope. After the left anterior chest incised, the pectoralis major and the pectoralis minor were pulled and maintained to expose intercostal muscles. After making an incision in intercostal muscles in the $4^{th}$ intercostal space, the visual field was extended with a retractor, and the heart was checked. After the pericardium was incised, the heart was turned counterclockwise, running of the left coronary artery was checked, and an instrumental knot was formed using an 8-0 silk suture from the lower edge of the left atrial appendage to a distal of about 0.5 mm. When the change in color of the myocardium at the ligation distal from red to white after the coronary artery ligation was confirmed, creation of MT was confirmed. Then, the wound was sutured with a 4-0 silk, and the operation was completed.

The control group mice underwent the Sham operation. This was performed by removing the left coronary artery ligation from the above series of procedures.

After the operation, waiting was performed while keeping the mice warm on a heat retaining pad at 37° C. until the mice were recovered from anesthesia. The time until extubation was set to 4 hours at which the mice were fully awake and spontaneous respiration was stable and resumed, and there was little postoperative acute death. The operation time was 10 to 15 minutes, and the thoracotomy time was about 5 minutes.

Subsequent experiments were performed using mice in which MI was caused as a heart failure (HF) group and mice underwent the sham operation as a control group.

Echocardiography was performed on the HF model mice and the control mice at 28 days after the operation, and the heart rate (HR: bpm), the left ventricular end-diastolic dimension (LVDd: mm), the left ventricular end-systolic dimension (LVDs: mm), the left ventricular anterior wall thickness (LVAWT: mm), the left ventricular posterior wall thickness (LVPWT: mm), and the left ventricular fractional shortening (% FS) were measured. The results are shown in Table 1. In addition, compared to the control mice, in the HF model mice, the cardiac function significantly deteriorated, and the weight of the heart and lung significantly increased.

TABLE 1

|  | Control | HF |
| --- | --- | --- |
| HR (bpm) | 650.44 ± 17.75 | 693.36 ± 13.88 |
| LVDd (mm) | 3.29 ± 0.08 | 5.57 ± 0.16* |
| LVDs (mm) | 1.59 ± 0.07 | 4.84 ± 0.14* |
| % FS | 51.63 ± 1.80 | 13.19 ± 1.01* |
| LVAWT (mm) | 0.82 ± 0.03 | 0.44 ± 0.03* |
| LVPWT (mm) | 0.79 ± 0.02 | 1.09 ± 0.05* |

*$p < 0.05$ vs. Control

Figure 2:
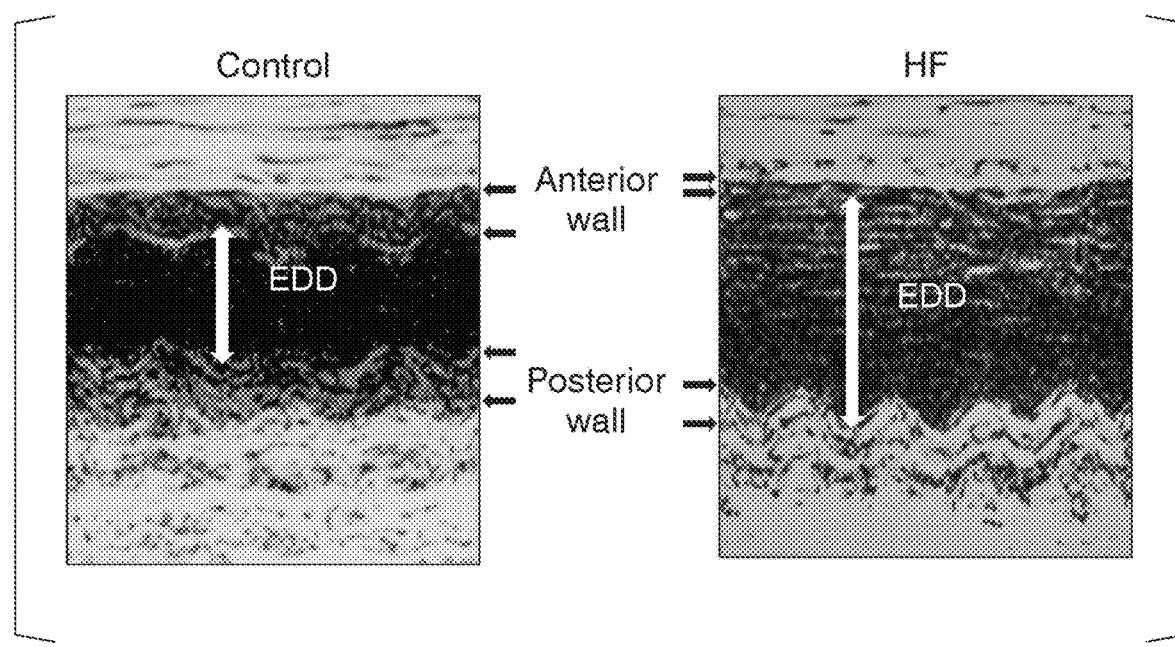
FIG. 2 shows diagrams of echo data of HF model mice and control mice in Reference Example 1.

In addition, FIG. 1 shows survival curves of HF model mice and control mice. The survival rate (%) of the HF model mouse group 3 to 4 weeks after myocardial infarction was significantly lower than that of the control mouse group and was about 50%. In addition, FIG. 2 shows echo data at 28 days after the operation of the HF model mice and the control mice. In the HF model mice, the anterior wall of the left ventricle was thinned and the posterior wall was enlarged in a compensation manner. In addition, the end-diastolic diameter (EDD) was also large.

Among the mitochondrial proteins in the myocardium fibrous tissues of the HF model mice and the control mice, the contents of Aconitase 2, VDAC (voltage-dependent anion-selective channel), MTCO1, Tom20, and COX IV (cytochrome c oxidase complex IV) were compared by immunoblotting. Immunoblotting was performed by western blotting using anti-Aconitase2 rabbit polyclonal antibodies (1:1,000, ab71440, commercially available from Abcam), anti-VDAC rabbit polyclonal antibodies (1:1,000, #4866, commercially available from CST), anti-MTCO1 mouse monoclonal antibodies (1:1,000, ab14705, commercially available from Abcam), anti-Tom20 rabbit monoclonal antibodies (1:1,000, ab186734, commercially available from Abcam), and anti-COX IV rabbit polyclonal antibodies (1:2,000, ab16056, commercially available from Abcam).

Figure 3:
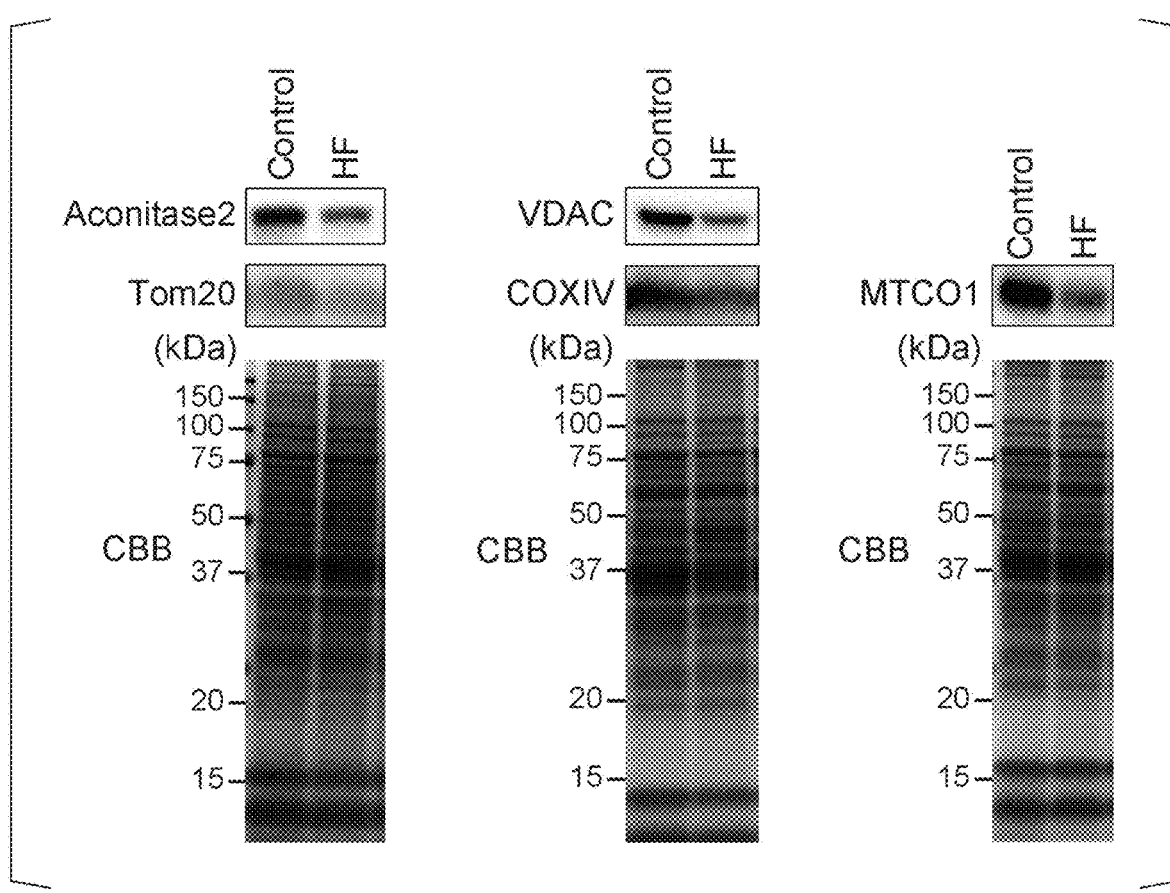
FIG. 3 shows diagrams of the results of western blotting of mitochondrial proteins in the myocardium of HF model mice and control mice in Reference Example 1.
Figure 4:
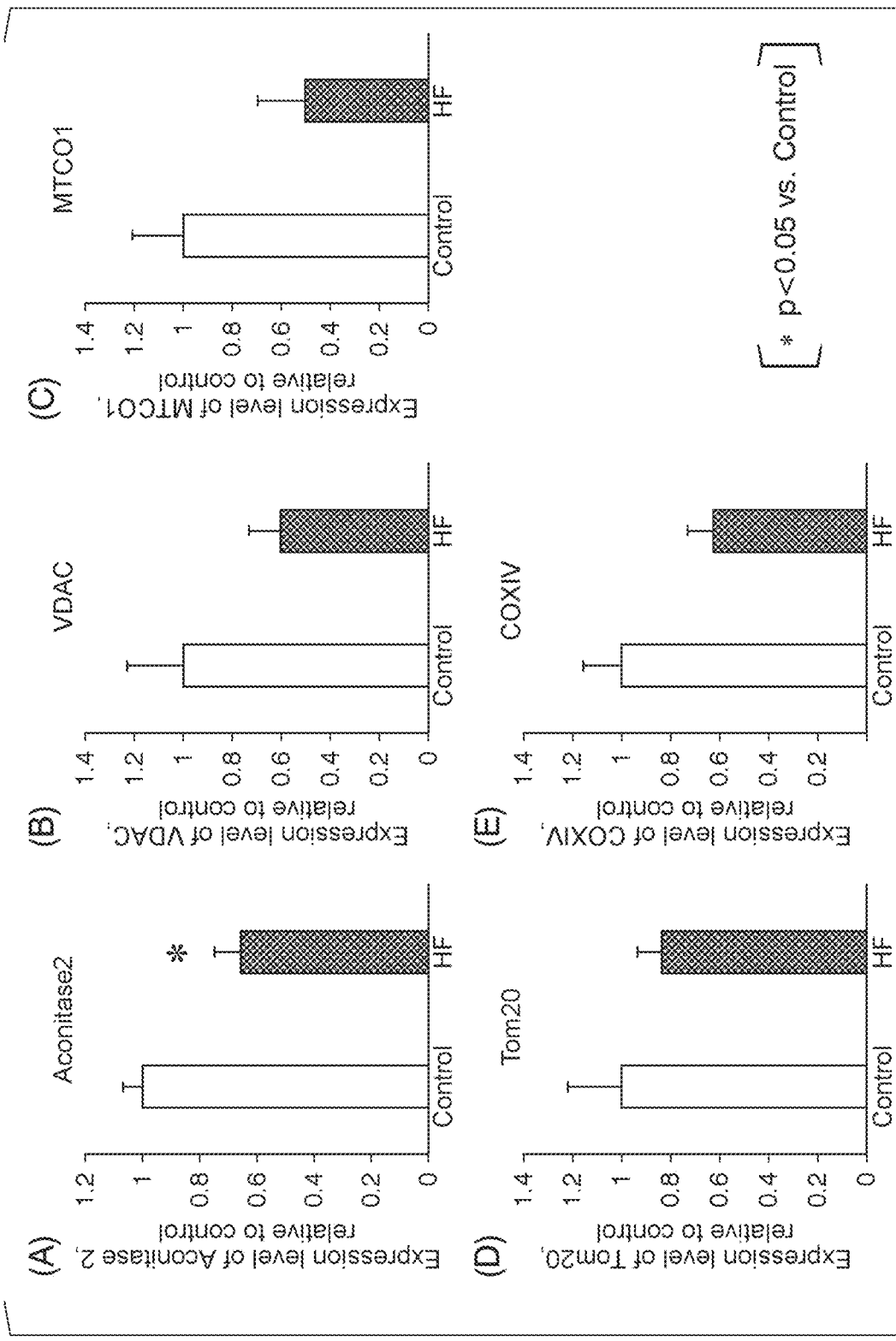
FIG. 4 shows diagrams of the measurement results of relative contents of mitochondrial proteins in the myocardium of HF model mice and control mice in Reference Example 1.

FIG. 3 shows the results of western blotting of mitochondrial proteins. In addition, FIG. 4 shows the measurement results of the relative content (the content of the control mice was set as 1) of respective mitochondrial proteins calculated based on the band intensity in western blotting in FIG. 3. It was confirmed that the content of all of the mitochondrial proteins decreased in the myocardium of the HF model mice, and the amount of mitochondria decreased in the myocardium of the HF model mice.

Example 1

The HF model mice were analyzed and the relationship between pathological conditions of heart failure and functions of mitochondrial complexes was examined.

Figure 5:
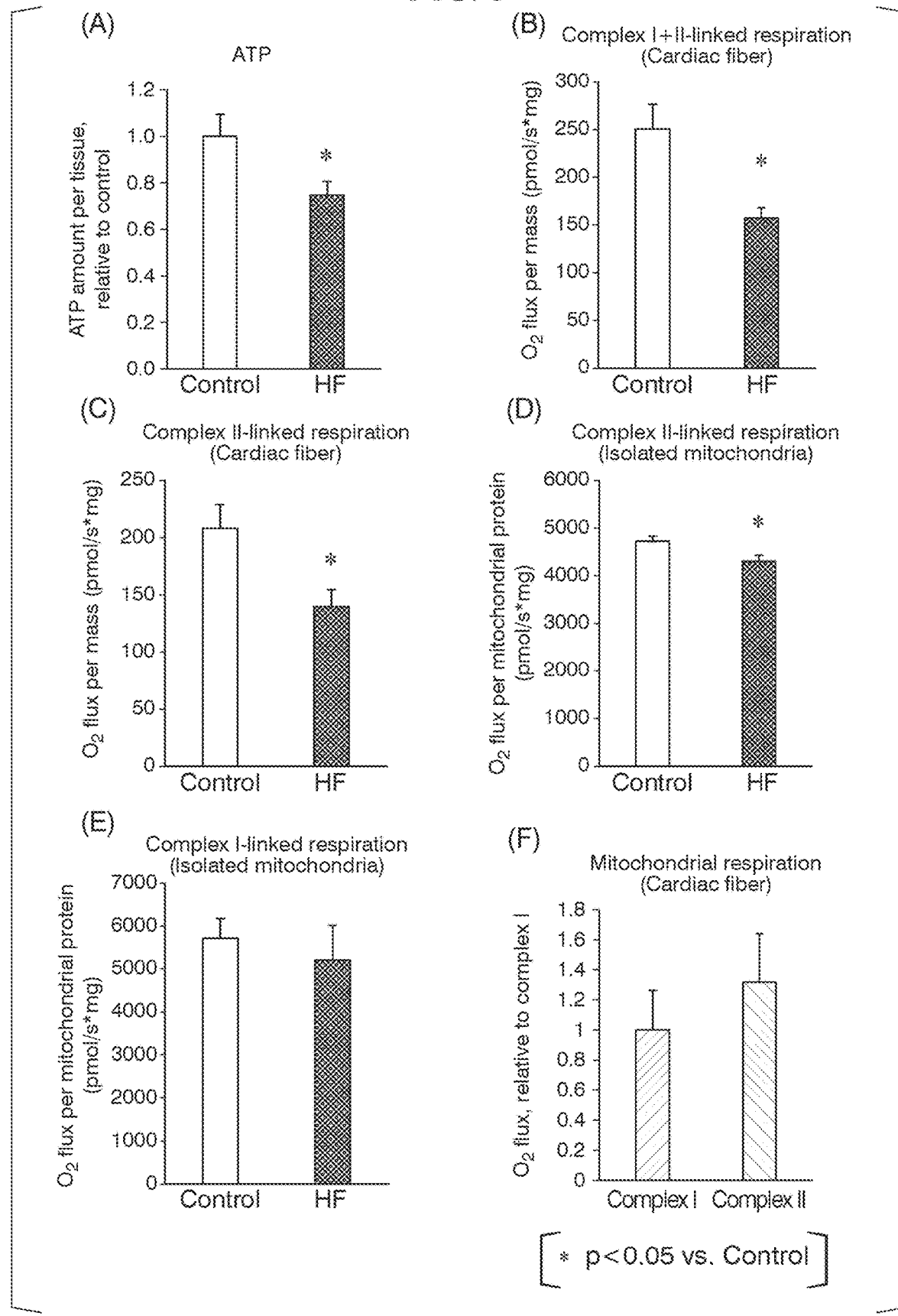
FIG. 5(A) is a diagram showing the measurement results of the amount of ATP in myocardium fibrous tissues of HF model mice and control mice.
FIG. 5(B) is a diagram showing the measurement results of the respiratory capacity (CI+II_OXPHOS) related to mitochondrial complex I and mitochondrial complex II in myocardium fibrous tissues.
FIG. 5(C) is a diagram showing the measurement results of the respiratory capacity (CII_OXPHOS) related to mitochondrial complex II in myocardium fibrous tissues.
FIG. 5(D) is a diagram showing the measurement results of the respiratory capacity (CII_OXPHOS) related to mitochondrial complex II in mitochondria isolated from the heart.
FIG. 5(E) is a diagram showing the measurement results of the respiratory capacity (CII_OXPHOS) related to mitochondrial complex I in mitochondria isolated from the heart, in Example 1
FIG. 5(F) is a diagram showing the measurement results of the respiratory capacity of mitochondrial complex I and mitochondrial complex II in myocardium fibrous tissues of control mice.

First, myocardium fibrous tissues were collected from the HF model mice and the control mice, and the amount of ATP in myocardium fibrous tissues, the respiratory capacity (CI+II_OXPHOS) related to mitochondrial complex I and mitochondrial complex II, the respiratory capacity (CII_OXPHOS) related to mitochondrial complex II, and the respiratory capacity (CI_OXPHOS) related to mitochondrial complex II in the mitochondria isolated from the heart and the respiratory capacity (CI_OXPHOS) related to mitochondrial complex I were measured. In addition, for the myocardial tissues of the control mice, the respiratory capacity related to mitochondrial complex I was compared with the respiratory capacity related to mitochondrial complex II. The results are shown in FIG. 5. In the HF model mice, the amount of ATP in the myocardium deceased (FIG. 5(A)), and the respiratory capacity (CI+II_OXPHOS) related to mitochondrial complex I and mitochondrial complex II also decreased (FIG. 5(B)). The respiratory capacity related to mitochondrial complex I was not different between the HF model mice and the control mice (FIG. 5(E)), but the respiratory capacity related to mitochondrial complex II was lower in the HF model mice than in the control mice (FIGS. 5(C) and 5(D)). For example, CII_OXPHOS was 4,724 µmol/s/mg in the control mouse group, but it was 4,306 µmol/s/mg in the HF model mouse group (P<0.05, FIG. 5(C)). In addition, originally, in the myocardium, the mitochondrial function was more improved in mitochondrial complex II than in mitochondrial complex I (FIG. 5(F)). Therefore, it was suggested that the decrease in the amount of ATP in the myocardium was due to deterioration of the function of mitochondrial complex II.

Figure 6:
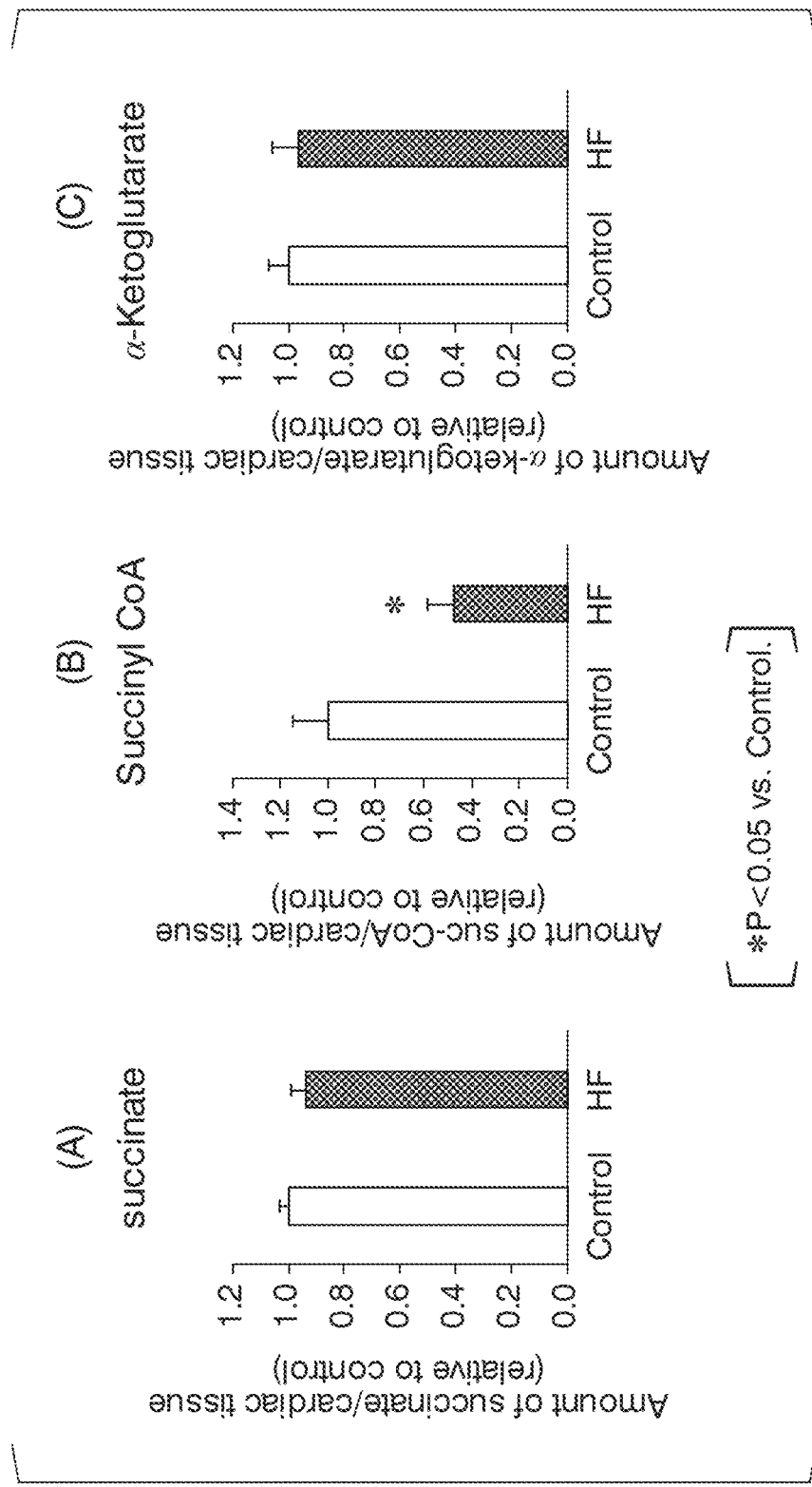
FIG. 6 shows diagrams of the measurement results of the relative contents of succinate (A), succinyl-CoA (B), and α-ketoglutaric acid (C) in myocardial tissues of HF model mice and control mice in Example 1.

Next, the contents of succinate, succinyl-CoA, and α-ketoglutaric acid in the myocardium fibrous tissues of each mouse were measured by liquid chromatography mass spectrometry. FIG. 6 shows the results of the relative contents of respective components when the content of the control mice was set as 1 (n=6). As a result, the amount of succinate and the amount of α-ketoglutaric acid were not different between the HF mice and the control mice, but the amount of succinyl-CoA was significantly lower in the HF mice than in the control mice. Succinyl-CoA provided succinic acid to mitochondrial complex II, and thus it was inferred that the complex II-linked respiration measured by a high-resolution respiration measurement method under a condition in which succinate (substrate of mitochondrial complex II) was saturated was significantly lower in the HF model mice (FIGS. 1(C) and 1(D)).

In order to examine the cause of decrease in the amount of succinate, the amount of SUCLA2 and SUCLG11 in mitochondria isolated from the myocardium of each mouse was examined. SUCLA2 and SUCLG1 are enzymes that convert succinyl-CoA into succinic acid and CoA in the TCA cycle.

Figure 7:
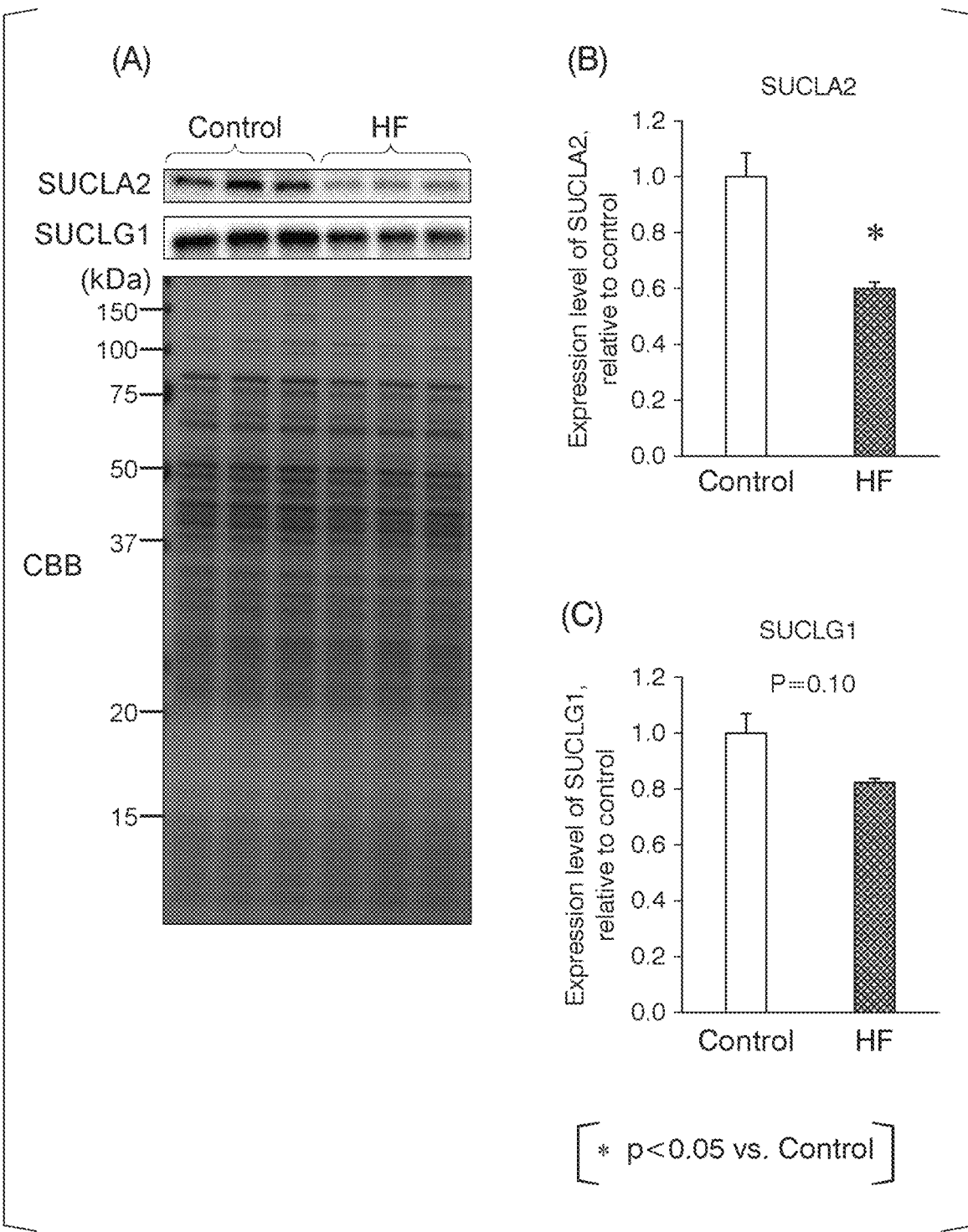
FIG. 7(A) is a diagram showing the results of western blotting of mitochondrial proteins isolated from the myocardium of HF model mice and control mice.
FIG. 7(B) is a diagram showing the measurement results of the relative content of SUCLA2.
FIG. 7(C) is a diagram showing the measurement results of the relative content of SUCLG1, in Example 1.

Specifically, the mitochondrial proteins isolated from the myocardium of each mouse were electrophoresed and then transferred to a PVDF membrane, western blotting was performed using anti-SUCLA2 rabbit monoclonal antibodies (1:1,000, ab202582, commercially available from Abcam) and anti-SUCLG1 rabbit polyclonal antibodies (1:1,000, ab204432, commercially available from Abcam), the concentration was measured based on the staining intensity of each protein band, and the relative content when the content of SUCLA2 and SUCLG1 in the control mice was set as 1 was calculated. The measurement results are shown in FIG. 7 (n=6). The expression level of these succinyl-CoA synthases decreased in the HF model mice, and it was confirmed that the decrease in the amount of succinate in the HF model mice was not due to the increased amount of these enzymes.

Figure 8:
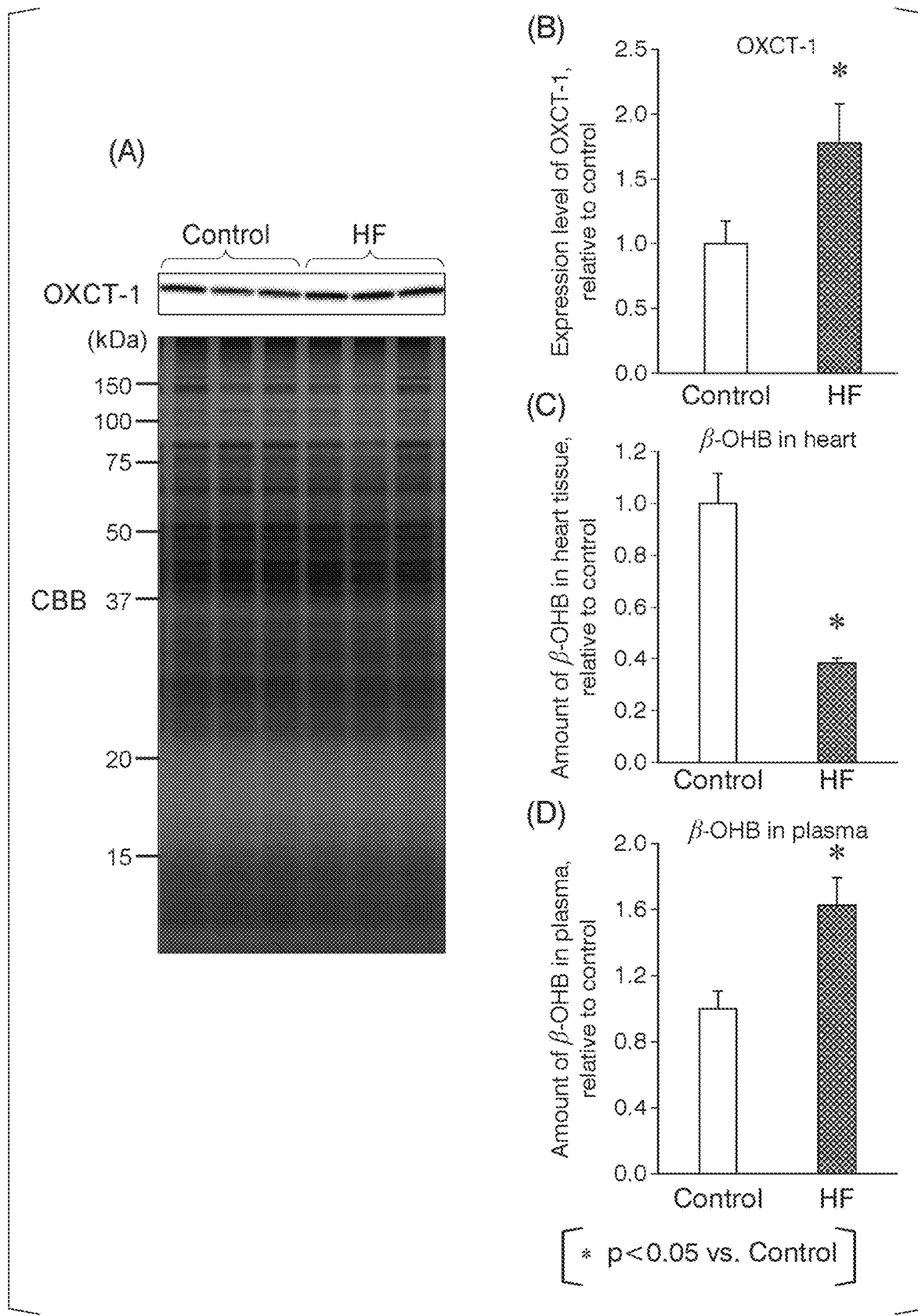
FIG. 8(A) is a diagram showing the results of western blotting of mitochondrial proteins isolated from the myocardium of HF model mice and control mice.
FIG. 8(B) is a diagram showing the measurement results of the relative content of OXCT-1 in mitochondria.
FIG. 8(C) is a diagram showing the measurement results of the relative content of β-OHB in the myocardium.
FIG. 8(D) is a diagram showing the measurement results of the relative content of β-OHB in plasma, in Example 1.

In ketone metabolism, when 3-ketoacid coenzyme A transferase (OXCT-1) produces acetoacetyl CoA from acetoacetate, it converts succinyl-CoA as a CoA supply source into succinate. Therefore, the amount of OXCT-1 in the mitochondria isolated from the myocardium of each mouse and the amount of β-OHB in the myocardium and plasma were examined, and the relative content when the content thereof in the control mice was set as 1 was obtained. The measurement results are shown in FIG. 8 (n=4 to 12). Compared to the control mice, in the HF model mice, the expression level per mitochondrion of OXCT-1 significantly increased. In addition, the amount of β-OHB in the HF model mice decreased in the myocardial tissues and increased in blood. The increased expression level of OXCT-1, which is an important protein for ketone synthesis suggested that ketone metabolism was enhanced in the HF model mice, and thus the amount of succinyl-CoA decreased.

Figure 9:
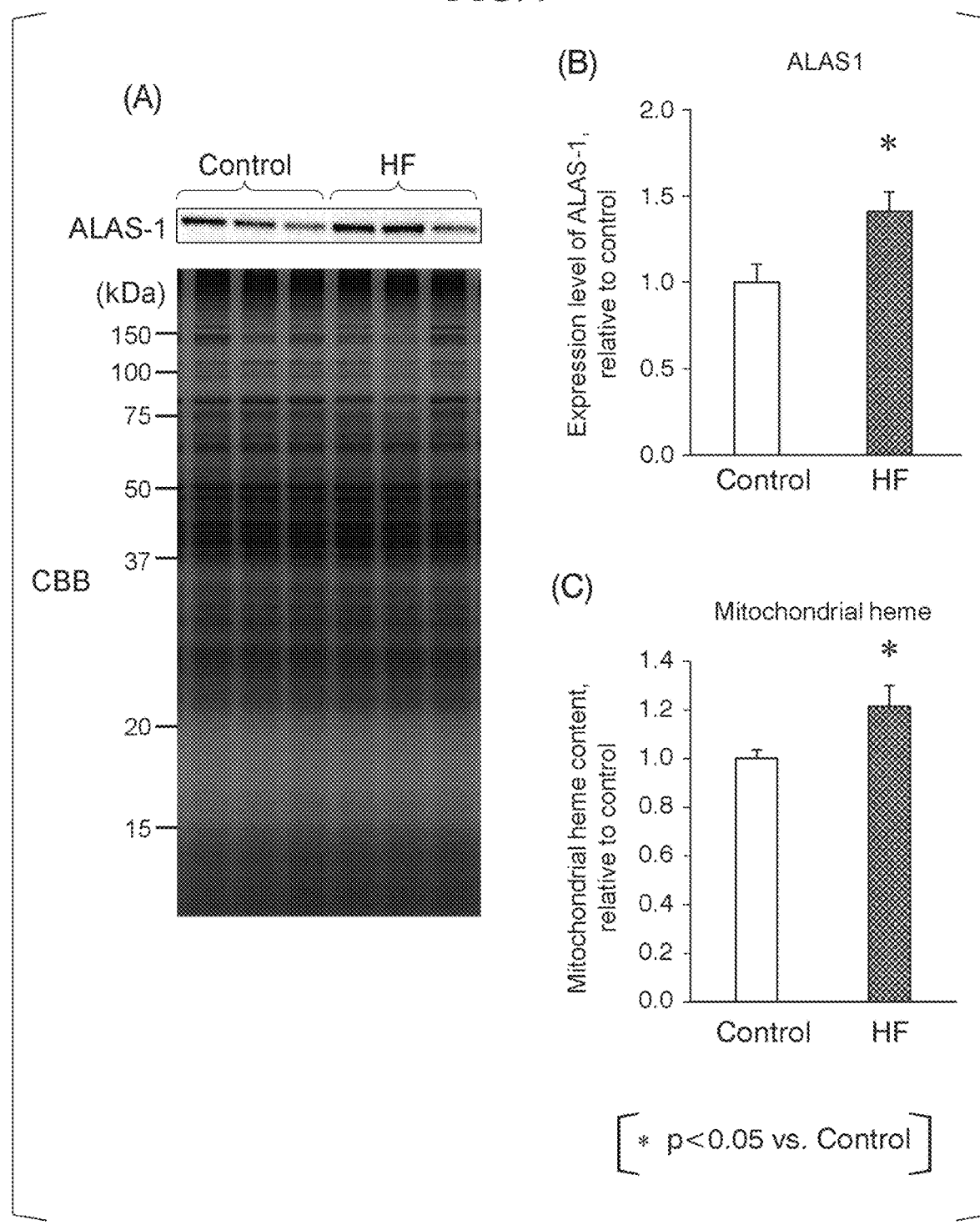
FIG. 9(A) is a diagram showing the results of western blotting of mitochondrial proteins isolated from the myocardium of HF model mice and control mice.
FIG. 9(B) is a diagram showing the measurement results of the relative content of ALAS1 in mitochondria.
FIG. 9(C) is a diagram showing the measurement results of the relative content of mitochondrial heme, in Example 1.

Succinyl-CoA also involved in heme synthesis. The reaction in the early stage of heme synthesis was caused in the mitochondria, and ALA was synthesized from glycine and succinyl-CoA with 5-aminolevulinic acid synthase (ALAS). Therefore, the amount of ALAS in the myocardium of each mouse and the amount of mitochondrial heme were examined, and the relative content when the content thereof in the control mice was set as 1 was obtained. The measurement results are shown in FIG. 9 (n=6). Compared to the control mice, in the HF model mice, the expression level of ALAS and the amount of mitochondrial heme were significantly increased. The increased expression level of ALAS, which is an important protein for heme synthesis suggested that succinyl-CoA may be consumed and reduced in the HF model mice due to enhanced ketone metabolism and heme synthesis.

Figure 10:
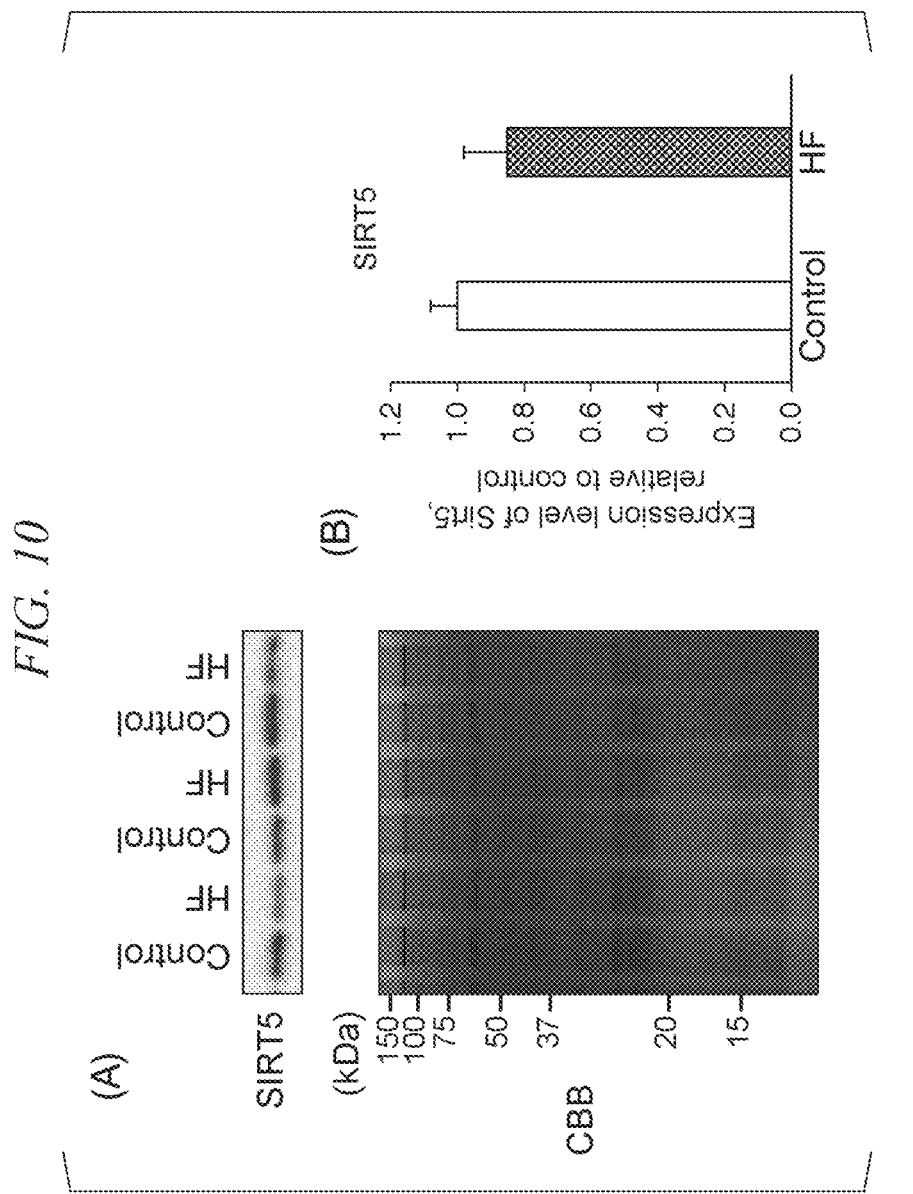
FIG. 10(A) is a diagram showing the results of western blotting of mitochondrial proteins isolated from the myocardium of HF model mice and control mice.
FIG. 10(B) is a diagram showing the measurement results of the relative content of SIRT5 in mitochondria, in Example 1.

In addition, succinylation was one of post-translational modifications of proteins, and was thought to be controlled by proteins that act on desuccinylation such as sirtuin 5 (SIRT5) and succinyl-CoA. Succinyl-CoA was a donor of succinyl groups for lysine residues and on the other hand, it was desuccinylated with SIRT5. Therefore, the amount of SIRT5 in the myocardium of each mouse was examined, and the relative content when the content thereof in the control mice was set as 1 was obtained. The measurement results are shown in FIG. 10 (n=3 to 10). There was no significant difference in the expression level of SIRT5 between the HF model mice and the control mice. Based on these results, it was thought that the decrease in succinylation in the HF model mice was not due to the enhanced function of SIRT5 but due to the decreased amount of succinyl-CoA.

Next, it was examined whether succinylation with mitochondrial proteins and functions of mitochondrial complex II could be improved by supplementing succinyl-CoA.

Figure 11:
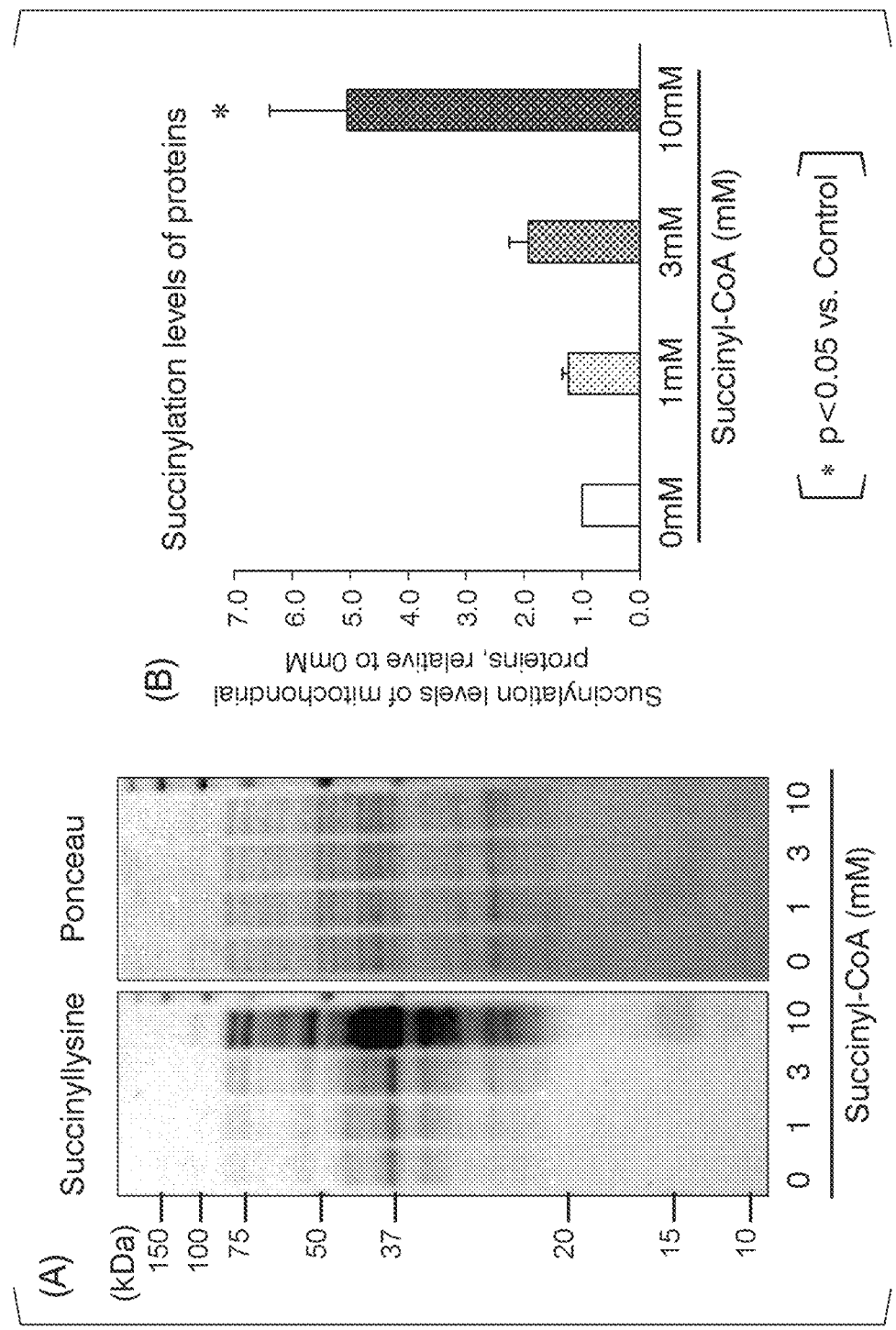
FIG. 11(A) is a diagram showing the results of western blotting of proteins after mitochondrial proteins isolated from the left ventricle of wild type mice were incubated in the presence of succinyl-CoA with various concentrations.
FIG. 11(B) is a diagram showing the measurement results of the succinylation level of mitochondrial proteins, in Example 1.

Specifically, first, succinyl-CoA (0, 1, 3, or 10 mM) was added to the mitochondria collected from the left ventricle of wild type mice (C57BL/6J), succinylation assay was performed, and the succinylation level of the mitochondrial proteins (the relative amount when the amount of succinylation proteins without addition of succinyl-CoA (0 mM) was set as 1) was examined. The results are shown in FIG. 11 (n=3 to 19). As a result, it was found that, when succinyl-CoA was added to the mitochondria isolated from the myocardium of mice, succinylation in the mitochondrial protein increased.

Figure 12:
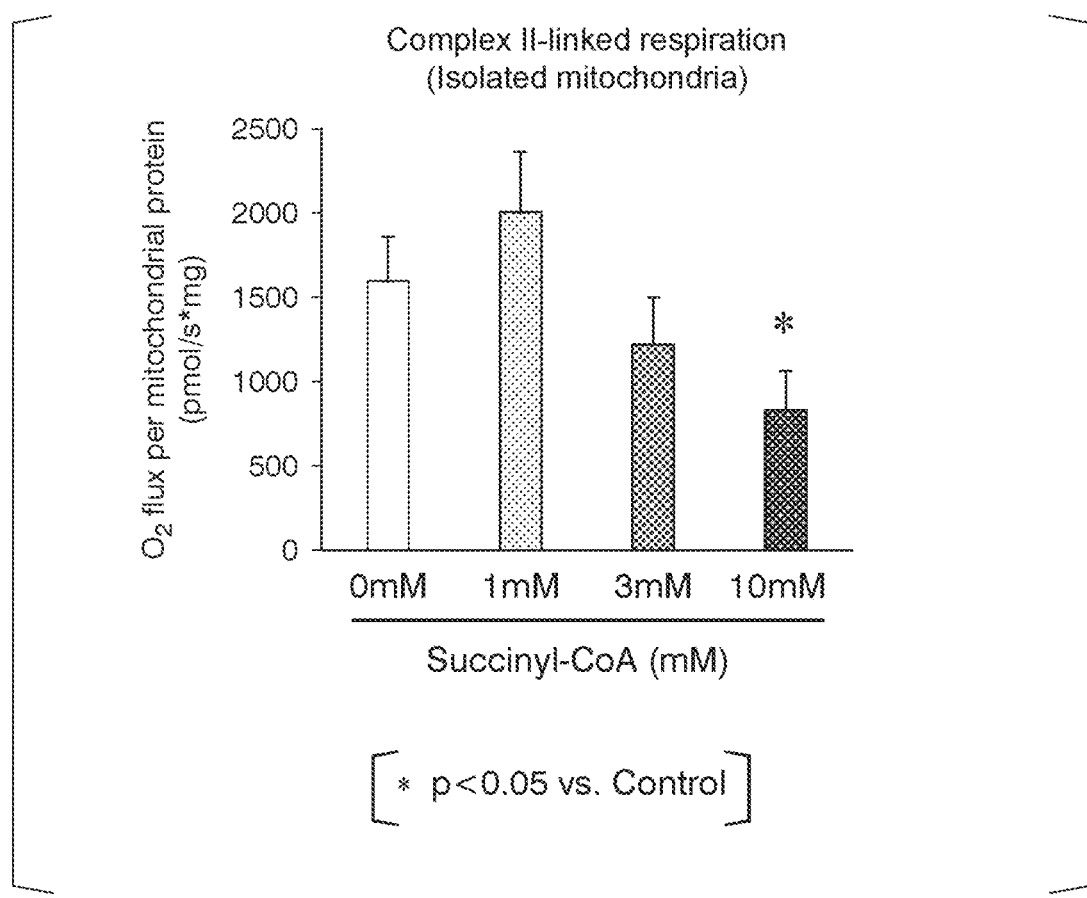
FIG. 12 is a diagram showing the measurement results of the respiratory capacity related to mitochondrial complex II of mitochondria isolated from the left ventricle of wild type mice in Example 1.

In addition, succinyl-CoA (0, 1, 3, or 10 mM) was added to the mitochondria isolated from wild type mice, succinylation assay was performed, and the respiratory capacity related to mitochondria was examined. The results are shown in FIG. 12 (n=3 to 19). Interestingly, the respiratory capacity related to mitochondrial complex II significantly decreased when 10 mM succinyl-CoA was added to the mitochondria, but it conversely increased when 1 mM succinyl-CoA was added. Accordingly, succinylation by addition of succinyl-CoA and the respiratory capacity related to mitochondrial complex II were bimodal, and excessive succinylation deteriorated functions of proteins, but it is thought that succinylation with addition of an appropriate amount of succinyl-CoA may be a necessary modification for proteins to function normally.

Figure 13:
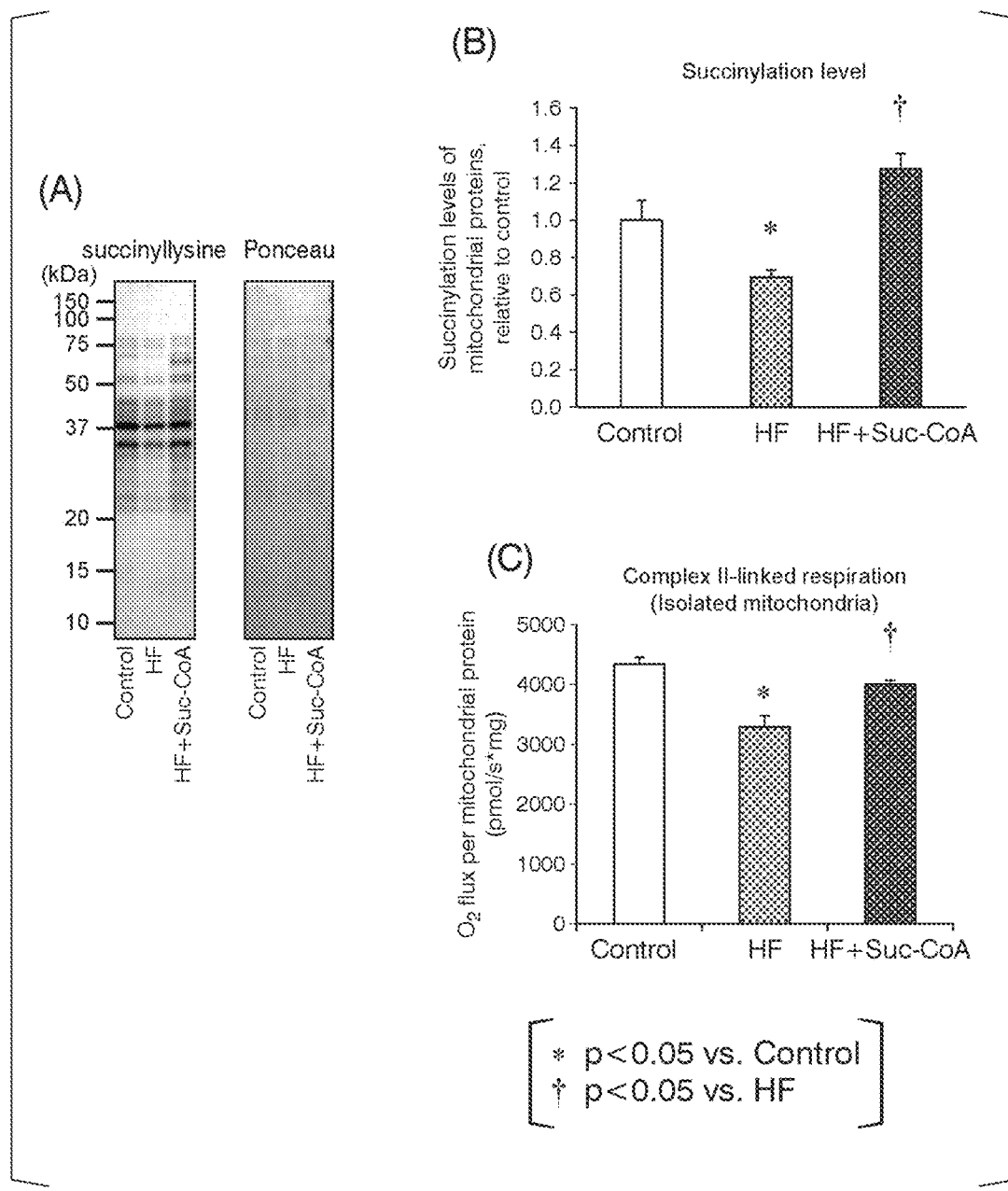
FIG. 13(A) is a diagram showing the results of western blotting of proteins after succinyl-CoA was added to mitochondria isolated from HF model mice and incubating was performed.
FIG. 13(B) is a diagram showing the measurement results of the succinylation level of mitochondrial proteins.
FIG. 13(C) is a diagram showing the measurement results of the respiratory capacity related to mitochondrial complex II, in Example 1.

0.1 mM succinyl-CoA was added to the mitochondria isolated from the HF model mice, succinylation assay was performed, and the succinylation level and the respiratory capacity related to mitochondrial complex II were examined. As a control, the same experiment was also performed for the control mice. The results are shown in FIG. 13 (n=3 to 10). In the HF model mice, the amount of succinyl-CoA decreased, and also both succinylation of mitochondrial proteins and the respiratory capacity related to mitochondrial complex II significantly decreased. This decrease in the succinylation level and the respiratory capacity related to mitochondrial complex II was improved when succinyl-CoA was added. The mitochondria isolated from the HF model mice and 0.1 mM succinyl-CoA were incubated together for 15 minutes, and thus the respiratory capacity related to mitochondrial complex II was improved from 3,291 μmol/s/mg to 4,037 μmol/s/mg (P<0.05. FIG. 13(C)).

Based on these results, it was confirmed that succinylation of mitochondrial proteins reduced due to heart failure and when succinyl-CoA was administered, the succinylation level and also the respiratory capacity related to mitochondrial complex II were improved. Thus, it was found that, since succinyl-CoA supplementation could improve deterioration of functions of mitochondrial complex II in the heart of the HF model mice, succinyl-CoA was a potential treatment target for mitochondrial dysfunction in patients with heart failure.

Figure 14:
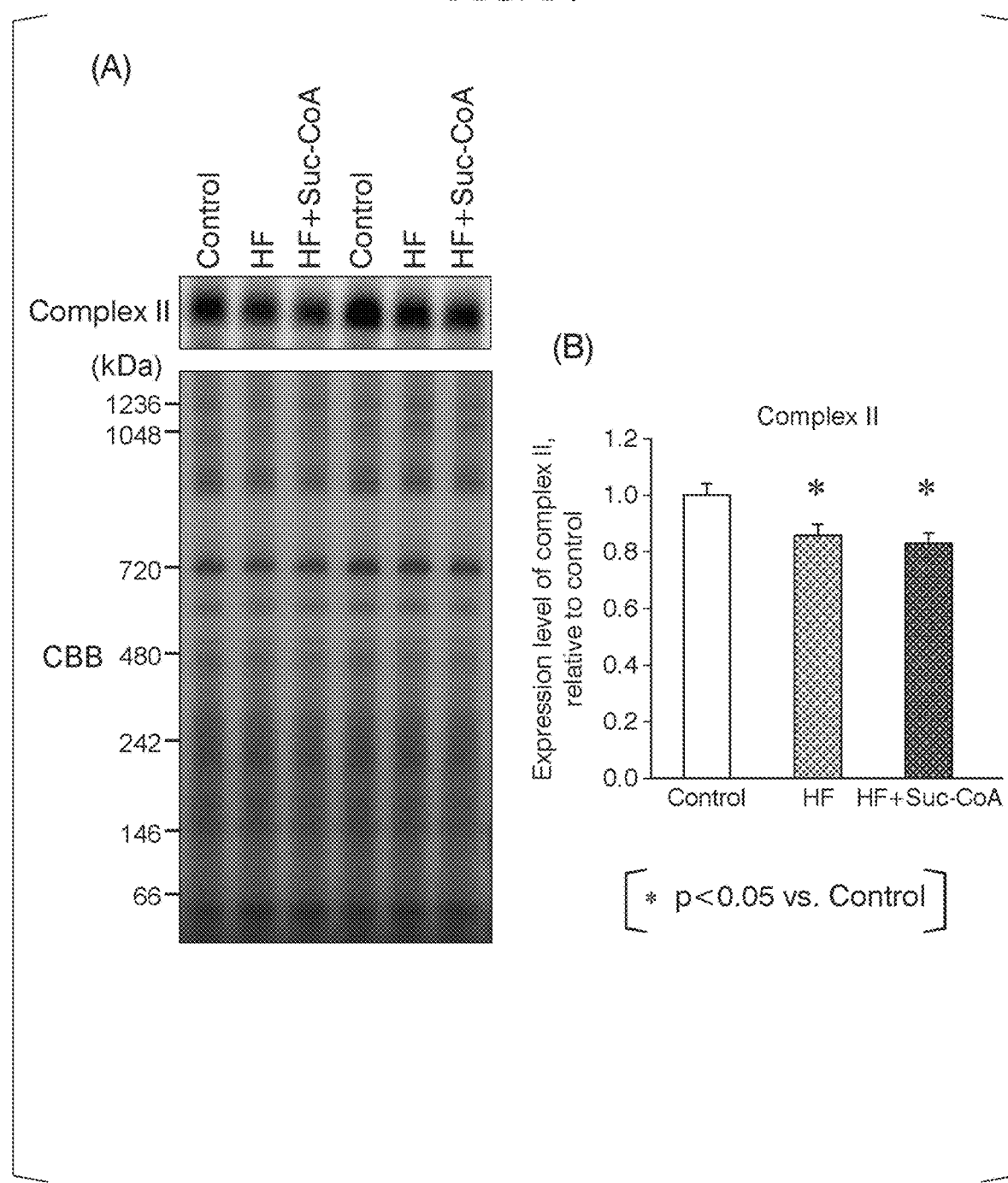
FIG. 14(A) is a diagram showing the results of western blotting of mitochondria isolated from control mice and HF model mice and mitochondrial proteins that were isolated from HF model mice and then treated with 1 mM succinyl-CoA and FIG. 14(B) is a diagram showing the measurement results of the respiratory capacity related to mitochondrial complex II, in Example 1.

Based on the results so far, it was clearly understood that the respiratory capacity related to mitochondrial complex II could be controlled by the expression level of mitochondrial complex II per mitochondrion. Therefore, for the mitochondria isolated from the control mice and the HF model mice and the mitochondria isolated from the HF model mice and then treated with 1 mM succinyl-CoA, the expression level of mitochondrial complex II per mitochondrion was evaluated using anti-SDHA mouse monoclonal antibodies (1:1, 000, ab14715, commercially available from Abcam) by a blue native method. The results are shown in FIG. 14 (n=6). The expression level of mitochondrial complex II per mitochondrion significantly decreased in the HF model mice. Even if succinyl-CoA was added to the mitochondria of the HF model mice, the amount of mitochondrial complex II remained reduced. Based on these results, it was found that the cause of dysfunction of mitochondrial complex II in the HF model mice was not the association of mitochondrial complex II.

Figure 15:
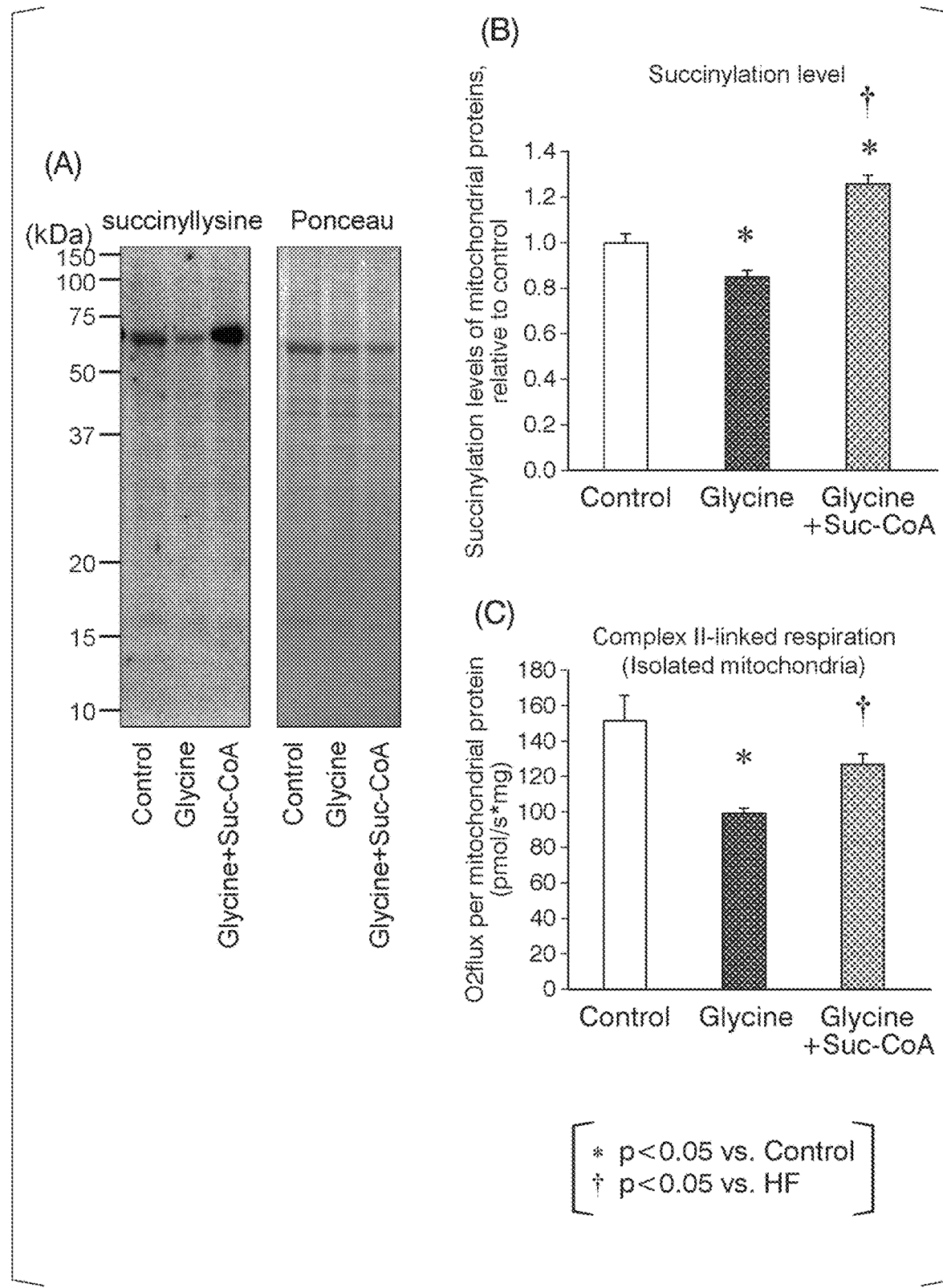
FIG. 15(A) is a diagram showing the results of western blotting of mitochondrial proteins of H9c2 cells treated with glycine or treated with glycine and succinyl-CoA
FIG. 15(B) is a diagram showing the measurement results of the succinylation level of mitochondrial proteins.
FIG. 15(C) is a diagram showing the measurement results of the respiratory capacity related to mitochondrial complex II, in Example 1.

In addition, in the heme synthesis process, glycine and succinyl-CoA reacted to synthesize ALA. Therefore, the relationship between this reaction process and the decrease in the amount of succinyl-CoA in heart failure was examined. The succinylation level and the respiratory capacity related to mitochondrial complex II were examined. The results are shown in FIG. 15 (n=4 to 8). When H9c2 cells were treated with glycine, as in the HF model mice, the succinylation level of mitochondrial proteins decreased. In addition, when treated with glycine and also succinyl-CoA was added, both the succinylation level and the respiratory capacity related to mitochondrial complex II were improved. Based on these results, it was suggested that decrease in succinylation was involved in dysfunction of mitochondrial complex II.

Example 2

In the initial reaction of the heme synthesis process, there was a reaction in which glycine and succinyl-CoA reacted to synthesize ALA. Therefore, an effect of supplementation of ALA on the myocardial mitochondrial function in the HF model mice was examined.

Specifically, after the HF model mice were underwent a left coronary artery ligation operation, an aqueous solution (50 mg/L) containing ALA (≥98%, commercially available from Sigma Aldrich) was administered by forced drinking (6 to 8 mg/kg/day), and on the $28^{th}$ day after the operation, the mitochondrial functions were measured using echocardiography and a mitochondrial respiratory capacity measurement device. As a control, echocardiography and mitochondrial function measurement were also performed on the control mice raised without administration of ALA.

Figure 16:
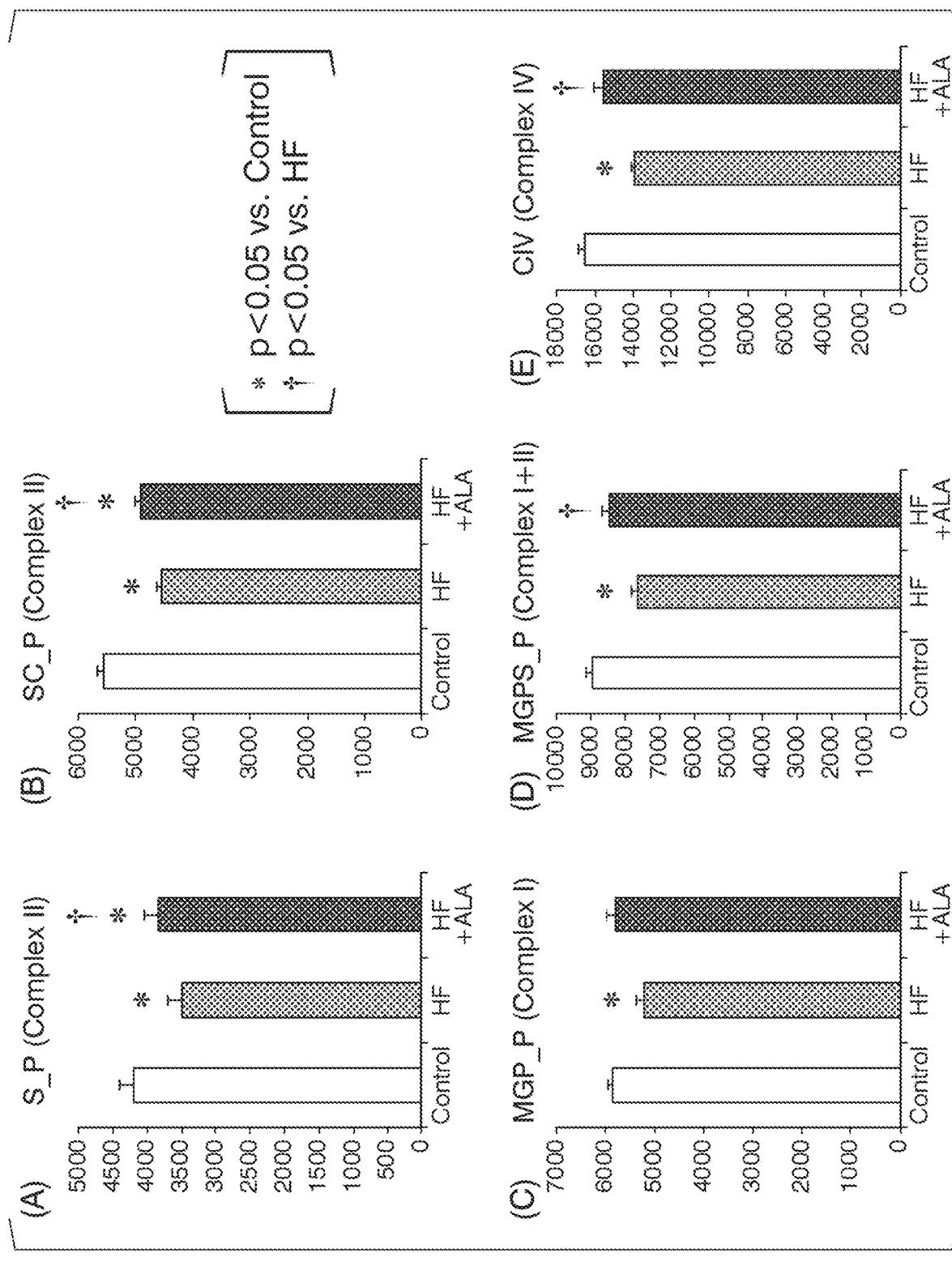
FIG. 16(A) is a diagram showing the measurement results of the respiratory capacity related to mitochondrial complex II after ALA was added to mitochondria isolated from HF model mice and incubating was performed.
FIG. 16(B) is a diagram showing the measurement results of the respiratory capacity related to mitochondrial complex II when succinic acid, which is a substrate of mitochondrial complex II, was loaded to a maximum.
FIG. 16(C) is a diagram showing the measurement results of the respiratory capacity related to mitochondrial complex I.
FIG. 16(D) is a diagram showing the measurement results of the respiratory capacity related to mitochondrial complex I and mitochondrial complex II.
FIG. 16(E) is a diagram showing the measurement results of the respiratory capacity related to mitochondrial complex IV, in Example 2.

Mitochondrial function measurement was performed on the mitochondria isolated from myocardium fibrous tissues collected from each mouse. The results of mitochondrial function measurement are shown in FIG. 16. FIG. 16(A) shows the measurement results of the respiratory capacity related to mitochondrial complex II, FIG. 16(B) shows the measurement results of the respiratory capacity related to mitochondrial complex II when succinic acid, which is a substrate of mitochondrial complex II, was loaded to a maximum, FIG. 16(C) shows the measurement results of the respiratory capacity related to mitochondrial complex I. FIG. 16(D) shows the measurement results of the respiratory capacity related to mitochondrial complex I and mitochondrial complex II, and FIG. 16(E) shows the measurement results of the respiratory capacity related to mitochondrial complex IV. As a result, it was confirmed that, in the mitochondria of the HF model mice, the respiratory capacity related to mitochondrial complex II, the respiratory capacity related to mitochondrial complex I and mitochondrial complex II, and the respiratory capacity related to mitochondrial complex IV were improved when ALA was administered.

Figure 17:
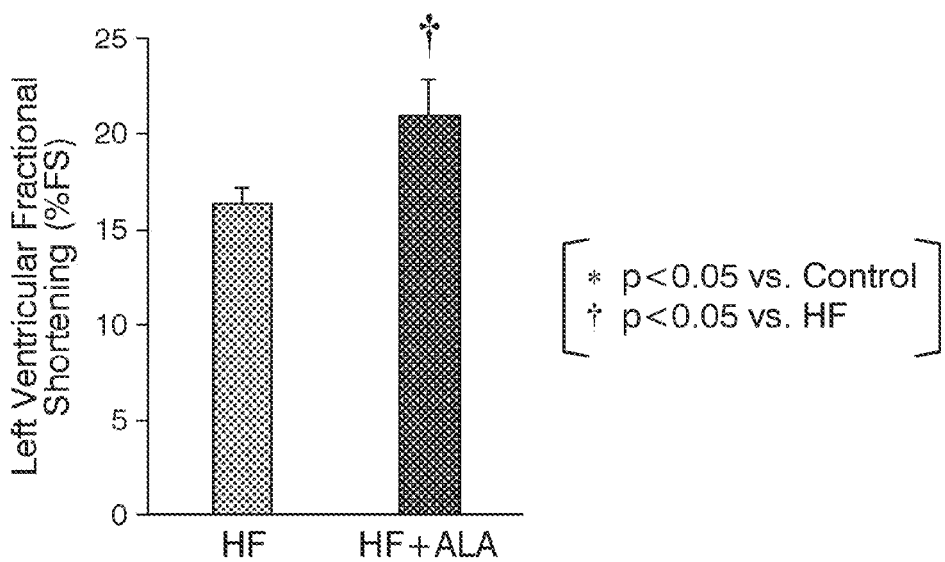
FIG. 17 is a diagram showing the measurement results of the left ventricular fractional shortening (% FS) obtained by performing echocardiography on HF model mice without administration of ALA and HF model mice to which ALA was administered in Example 2.

In addition, FIG. 17 shows the measurement results of the left ventricular fractional shortening (% FS) obtained by echocardiography for the HF model mice without administration of ALA and the HF model mice to which ALA was administered. As a result, it was confirmed that, in the HF model mice, according to administration of ALA, the left ventricular fractional shortening was significantly improved, and the cardiac function was improved.

Figure 18:
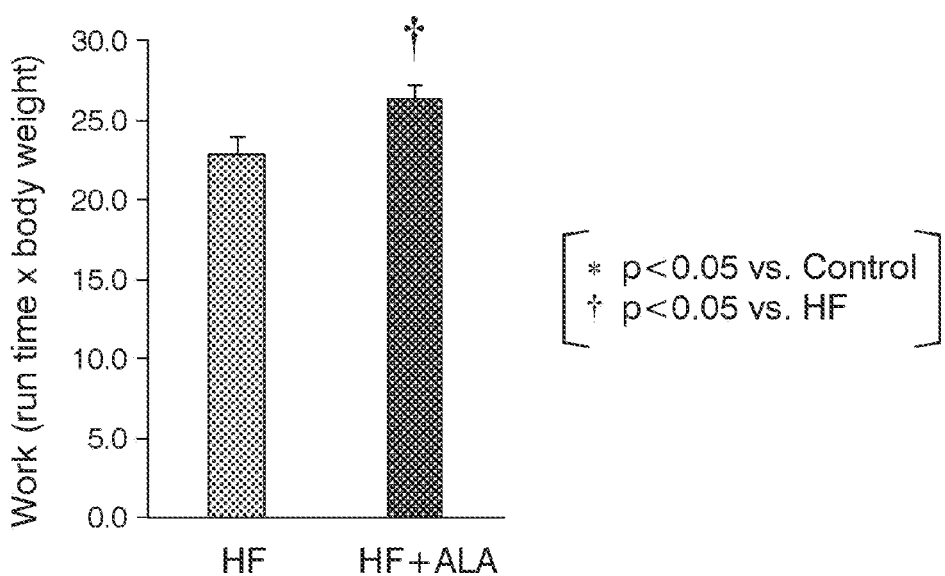
FIG. 18 is a diagram showing the measurement results of the exercise capacity (work time×body weight) of HF model mice without administration of ALA and HF model mice to which ALA was administered in Example 2.

In addition, the exercise capacities of the HF model mice without administration of ALA and the HF model mice to which ALA was administered were examined. The exercise capacity was expressed as a product of an exercise time and a body weight. The exercise time was measured using a small animal treadmill, and mice were at rest for 10 minutes, and w-up for 10 minutes (6 m/min, inclination of 10 degrees), and then forced to run until exhaustion by increasing a load (2 m/2 min). The results are shown in FIG. 18. As a result, in the HF model mice, the exercise capacity was significantly improved by administration of ALA. This is because the cardiac function was improved by administration of ALA.

When ALA was administered to the HF model mice, the respiratory capacity of the mitochondria in the myocardium was improved, and consequently the cardiac function was improved. Thus, it was found that ALA or its derivative could be an effective therapeutic agent for heart failure.

Example 31

In chronic HF patients, the amount of mitochondrial ROS released from PBMC and oxidative stress of mitochondria in PBMC were examined, and the effect on the severity of HF and exercise intolerance was examined.

36 chronic HF patients (62113 years old) were divided into two groups: mild heart failure group (NYHA I-II group: n=17) composed of patients with functional class I to II in New York Heart Association (NYHA) and severe heart failure group (NYHA III group: n=19) composed of patients with functional class III in NYHA. Table 2 shows information on each patient group.

TABLE 2

| | NYHA I-II (n = 17) | NYHA III (n = 19) | P-value |
|---|---|---|---|
| Age [years] | 61 ± 15 | 62 ± 13 | 0.765 |
| Male [n (%)] | 15 (88) | 16 (84) | 0.727 |
| BMI [kg/m$^2$] | 25.1 ± 4.0 | 24.1 ± 4.3 | 0.479 |
| Plasma BNP [pg/dL] | 93.4 ± 101.2 | 286.0 ± 251.0 | 0.007 |
| Echocardiography; LVDd [mm] | 56.4 ± 9.6 | 65.9 ± 10.7 | 0.010 |
| LVEF [%] | 45.0 ± 14.0 | 27.2 ± 5.8 | <0.001 |
| IVST [mm] | 8.9 ± 1.7 | 8.7 ± 1.8 | 0.676 |
| LVPWT [mm] | 8.5 ± 1.1 | 8.4 ± 1.5 | 0.915 |
| Cardiopulmonary exercise test; Peak VO$_2$ [ml/kg/min] | 19.5 ± 4.5 | 14.5 ± 4.0 | 0.003 |

Values are mean ± SD or n (%). BMI = body mass index; BNP = brain natriuretic peptide; LVEF = left ventricular ejection fraction; LVDd = left ventricular end-diastolic diameter; LVEF = left ventricular ejection fraction; IVST = interventricular septum thickness; LVPWT = left ventricular posterior wall thickness; VO2 = oxygen uptake.

In order to evaluate the exercise capacity of these patients, a cardiopulmonary exercise test using a bicycle ergometer was performed, and PBMCs were collected. The PBMCs collected from the patients were subjected to a cell membrane permeation treatment, and the mitochondrial respiratory capacity and the amount of ROS released were then measured. The amount of ROS was measured using fluorescence spectroscopy.

Figure 19:
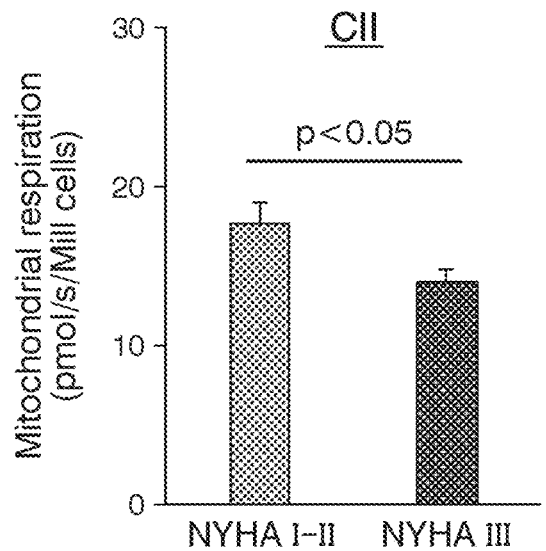
FIG. 19 is a diagram showing the measurement results of the respiratory capacity related to mitochondrial complex II of PBMC collected after a cardiopulmonary exercise test in a mild heart failure group (NYHA I-II group) and a severe heart failure group (NYHA III group) in Example 3.
Figure 20:
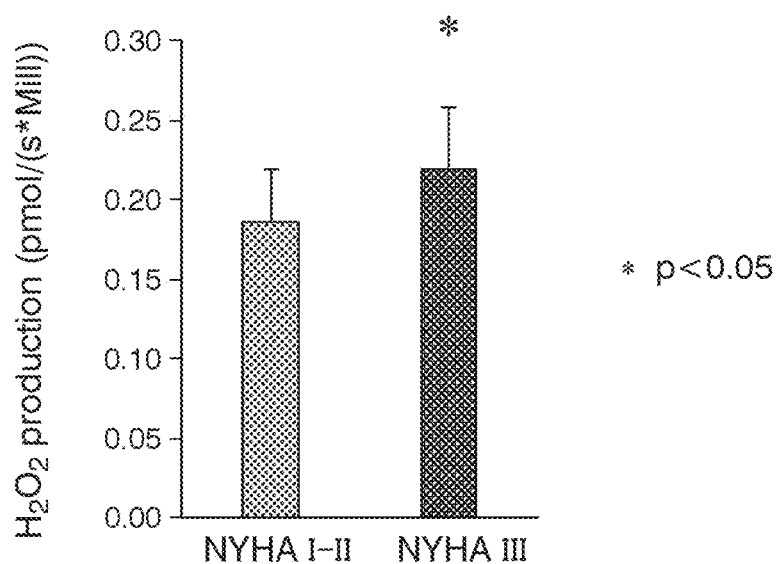
FIG. 20 is a diagram showing the measurement results of the amount of hydrogen peroxide released from PBMC collected after a cardiopulmonary exercise test in a mild heart failure group (NYHA I-II group) and a severe heart failure group (NYHA III group) in Example 3.

FIG. 19 shows the measurement results of the respiratory capacity related to mitochondrial complex II in PBMC in each group, and FIG. 20 shows the measurement results of the amount of hydrogen peroxide released from PBMC. The bars in FIG. 19 and FIG. 20 indicate average value±SD, and the asterisk indicates P value<0.05. In addition, the oxygen consumption amount in the drawing is the maximum respiratory capacity related to mitochondrial complex II (corresponding to the above "CII_ETS").

As shown in FIGS. 19 and 20, the respiratory capacity related to mitochondrial complex I, the respiratory capacity related to mitochondrial complex I+II and the respiratory capacity related to mitochondrial complex IV in PBMC after the oxidative stress were similar between the mild heart failure group and the severe heart failure group, but the maximum respiratory capacity related to mitochondrial complex II was significantly lower in the severe heart failure group than in the mild heart failure group. In addition, in the severe heart failure group, the amount of hydrogen peroxide (amount of ROS) released from the mitochondria in PBMC was very large. In addition, the plasma level of B-type natriuretic peptide (BNP), which is a biomarker for HF severity, was 286.0±251.0 µg/mL in the severe heart failure group, and 93.4±101.2 µg/mL in the mild heart failure group, and the level was significantly higher in the severe heart failure group than in the mild heart failure group (P<0.01). In addition, the peak oxygen uptake amount (VO$_2$) was 14.4±4.1 mL/kg/min in the severe heart failure group and 19.7±4.5 mL/kg/min in the mild heart failure group, and the amount was significantly lower in the severe heart failure group than in the mild heart failure group (P<0.01).

The maximum respiratory capacity related to mitochondrial complex II in PBMC was significantly reduced in the severe heart failure group in association with the decreased peak VO$_2$. In particular, in the severe heart failure group, the amount of mitochondrial ROS (hydrogen peroxide) released from PBMC was very large, and the amount of ROS released was closely correlated with an increase in plasma BNP levels and a decrease in peak VO$_2$.

Based on these results, it was found that the increased mitochondria oxidative stress, characterized by the increased amount of mitochondrial ROS released from PBMC, was related to the HF severity and exercise intolerance in chronic HF patients. In addition, similar to the HF model mice, also in HF patients, the respiratory capacity related to mitochondrial complex II decreased, and since this dysfunction of mitochondrial complex II was common, it was suggested that functions of mitochondrial complex II deteriorated in heart failure in general.

The invention claimed is:
1. A heart failure treatment method, comprising increasing an amount of succinyl-CoA in cardiomyocytes for an animal with heart failure.
2. The heart failure treatment method according to claim 1, wherein succinyl-CoA, 5-aminolevulinic acid, 5-aminolevulinic acid derivative, or pharmaceutically acceptable salt thereof is administered to the animal.
3. A heart failure treatment method, comprising:
evaluating the onset of heart failure according to the method of evaluating pathological conditions of heart failure comprising:
(i) measuring an amount of succinyl-CoA in cardiomyocytes collected from a test animal, a respiratory capacity of mitochondrial complex II in peripheral blood mononuclear cells collected from the test animal, or an amount of reactive oxygen species released from peripheral blood mononuclear cells collected from the test animal; and

(ii) evaluating the onset of heart failure of the test animal or the severity of heart failure based on the obtained measurement values; and increasing an amount of succinyl-CoA in cardiomyocytes of an animal evaluated as having a high likelihood of the onset of heart failure.

4. A method of evaluating a candidate compound for use as a heart failure treatment drug, comprising:

treating cells with glycine;

contacting the treated cells with the candidate compound and measuring an amount of succinyl-CoA in the cells; and evaluating usefulness of the candidate compound as a heart failure treatment drug based on the obtained measurement value.

5. The method of evaluating a candidate compound for use as a heart failure treatment drug according to claim 4, wherein the cells are myocardium-derived cultured cells.

6. A method of evaluating a candidate compound for use as a heart failure treatment drug, comprising:

treating cells with glycine;

contacting the treated cells with the candidate compound and measuring a respiratory capacity of mitochondrial complex II in the cells or an amount of reactive oxygen species released from the cells; and evaluating usefulness of the candidate compound as a heart failure treatment drug based on the obtained measurement value.

7. The method of claim 4, wherein the method further comprises treating a patient with heart failure comprising administering to the patient the candidate compound evaluated to be useful as a heart failure drug.

8. The method of claim 6, wherein the method further comprises treating a patient with heart failure comprising administering to the patient the candidate compound evaluated to be useful as a heart failure drug.

* * * * *